| (12) | United States Patent<br>Tabaru et al. | | (10) Patent No.: US 9,310,295 B2<br>(45) Date of Patent: Apr. 12, 2016 |
|---|---|---|---|

(54) LASER-TYPE GAS ANALYZER

(71) Applicant: FUJI ELECTRIC CO., LTD., Kawasaki-shi (JP)

(72) Inventors: Masaya Tabaru, Hino (JP); Kazuhiro Koizumi, Sagamihara (JP); Hideyuki Konishi, Hachioji (JP); Takashi Inui, Hachioji (JP)

(73) Assignee: FUJI ELECTRIC CO., LTD., Kawasaki-Shi (JP)

( * ) Notice: Subject to any disclaimer, the term of this patent is extended or adjusted under 35 U.S.C. 154(b) by 0 days.

(21) Appl. No.: 14/732,139

(22) Filed: Jun. 5, 2015

(65) Prior Publication Data

US 2015/0268159 A1    Sep. 24, 2015

Related U.S. Application Data

(63) Continuation of application No. PCT/JP2013/080634, filed on Nov. 13, 2013.

(30) Foreign Application Priority Data

Jan. 11, 2013    (JP) ................................. 2013-003511

(51) Int. Cl.
*G01N 21/3504*    (2014.01)
*G01N 21/39*    (2006.01)
(Continued)

(52) U.S. Cl.
CPC ........ *G01N 21/3504* (2013.01); *G01N 21/3103* (2013.01); *G01N 21/359* (2013.01); *G01N 21/39* (2013.01); *G01N 2201/0612* (2013.01)

(58) Field of Classification Search
CPC .......... G01N 21/3504; G01N 21/3103; G01N 21/359; G01N 2201/0612

USPC ............ 250/339.01, 343, 340, 338.1, 339.13, 250/339.12
See application file for complete search history.

(56) References Cited

U.S. PATENT DOCUMENTS 4,567,366 A      1/1986   Shinohara
7,217,121 B2 *   5/2007   Thomson .................. B08B 7/00
                                              250/339.01
(Continued)

FOREIGN PATENT DOCUMENTS

EP      2133686 A1    12/2009
JP      52106777 A     9/1977
(Continued)

OTHER PUBLICATIONS

International Search Report issued in PCT/JP2013/080634, mailed Feb. 10, 2014. English translation provided.

*Primary Examiner* — David Porta
*Assistant Examiner* — Djura Malevic
(74) *Attorney, Agent, or Firm* — Rossi, Kimms & McDowell LLP

(57) ABSTRACT

Aspects of a laser-type gas analyzer can include a mid-infrared light reception signal processing and computing unit that calculates a gas concentration of the first gas to be measured on the basis of a mid-infrared light reception signal, a near-infrared light reception signal processing and computing unit that detects, at respective times, the gas concentration of the second gas to be measured, water concentration in a space, and alight amount decrement due to dust, on the basis of near-infrared light reception signal. Also included can be a gas concentration correcting unit that corrects the gas concentrations of the first and second gases to be measured using the water concentration and the light amount decrement.

3 Claims, 14 Drawing Sheets

(51) Int. Cl.
*G01N 21/359* (2014.01)
*G01N 21/31* (2006.01)

(56) References Cited

U.S. PATENT DOCUMENTS

2004/0191712 A1* 9/2004 Thomson .................. B08B 7/00
431/12
2010/0188232 A1* 7/2010 Lambert ............ G01N 21/3504
340/573.1
2012/0287418 A1* 11/2012 Scherer .................. G01N 21/61
356/51
2013/0334419 A1* 12/2013 Kluczynski ............... G01J 3/42
250/339.13

FOREIGN PATENT DOCUMENTS

| JP | 60029642 A | 2/1985 |
| JP | 02159559 A | 6/1990 |
| JP | 07151681 A | 6/1995 |
| JP | 2005024251 A | 1/2005 |
| JP | 2009047677 A | 3/2009 |
| JP | 2010185694 A | 8/2010 |
| JP | 2013117517 A | 6/2013 |

* cited by examiner

LASER-TYPE GAS ANALYZER

CROSS-REFERENCE TO RELATED APPLICATIONS

This application is a continuation of International Application No. PCT/JP 2013/080634, filed on Nov. 13, 2013, which is based on and claims priority to Japanese Patent Application No. JP 2013-003511, filed on Jan. 11, 2013. The disclosure of the Japanese priority application and the PCT application in their entirety, including the drawings, claims, and the specification thereof, are incorporated herein by reference.

BACKGROUND

1. Field of the Invention

The present invention relates to a laser-type gas analyzer that measures, by laser light, the gas concentration of various types of gas in flues.

2. Related Art

As is known, gas atoms and molecules have unique optical absorption spectra. For instance, FIG. 20 illustrates the optical absorption spectrum of ammonia ($NH_3$). The abscissa axis of the graph represents wavelength, and the ordinate axis represents optical absorption intensity.

Laser-type gas analyzers are known as gas analyzers that detect the concentration of various types of gas by relying on such optical absorption spectra. In such analyzers, light emitted by a laser light source having an emission wavelength region identical to that of the optical absorption spectrum of the gas to be measured is irradiated to the gas to be measured, and the concentration of the gas is measured using the absorption of laser light by the molecules and atoms of the gas to be measured.

In a gas analyzer that utilizes laser light, the gas concentration is measured on the basis of the principle whereby optical absorption intensity at a specific wavelength is proportional to gas concentration. The attenuation amount of an absorption line at a central wavelength $\lambda_c$ is proportional to the gas concentration. Therefore, the gas concentration can be estimated by irradiating the gas with semiconductor laser light having an oscillation wavelength at $\lambda_c$, and by multiplying the corresponding attenuation amount by an appropriate coefficient.

Concentration measurement methods by gas analysis relying on laser light include mainly differential absorption methods and frequency modulation methods. In a differential absorption method, gas concentrations can ordinarily be measured by way of a comparatively simple configuration. In a frequency modulation method, by contrast, signal processing is complex, but it is possible to measure gas concentration with high sensitivity.

For instance, Patent literature 1 (Japanese Patent Application Publication No. H07-151681, title of the invention "Gas Concentration Measurement Device") discloses a device that measures gas concentration in accordance with a differential absorption method. As illustrated in FIG. 8 of Patent literature 1, this gas concentration measurement device is provided with a two-wavelength type semiconductor laser, a gas cell, a light-receiving lens, a light-receiving unit and a gas concentration measurement device.

As illustrated also in the concentration measurement principle according to a differential absorption method of FIG. 21, a gas is irradiated with two kinds of laser light, namely laser light the oscillation wavelength whereof is set to the central wavelength $\lambda_c$ of the respective absorption line, and laser light the oscillation wavelength whereof is set to the central wavelength $\lambda_r$ of a wavelength without absorption line; then, a signal intensity difference obtained in the form of the difference in the intensities of signals outputted by respective light-receiving units is converted to concentration through multiplication by appropriate proportionality constants.

For instance, Patent literature 1 above discloses also a device that measures gas concentration according to a frequency modulation method. As illustrated in FIG. 7 of Patent literature 1, this gas concentration measurement device is provided with a frequency modulation-type semiconductor laser, a gas cell, a light-receiving lens, a light-receiving unit and a gas concentration measurement device.

As illustrated in the concentration measurement principle according to a frequency modulation method in FIG. 22, the output of a semiconductor laser is frequency-modulated at a central wavelength $\lambda_c$ with a modulation frequency $f_m$, and is irradiated to a gas to be measured, as a target. Absorption lines of gases behave substantially as a quadratic function with respect to frequency. Therefore, the absorption lines fulfill the role of a discriminator, and a signal (second harmonic signal) of a frequency twice the modulation frequency $f_m$ is obtained in the light-receiving unit. It becomes thus possible to estimate a fundamental wave by amplitude modulation, through envelope detection in the light-receiving unit, and to obtain a value proportional to gas concentration, through phase synchronization of the ratio of the amplitude of the fundamental and the amplitude of the second harmonic.

For instance, FIG. 23 illustrates a laser-type gas analyzer as a conventional gas analyzer that utilizes laser light. This laser-type gas analyzer is disclosed in Patent literature 2 (Japanese Patent Application Publication No. 2009-47677, title of the invention "Laser-Type Gas Analyzer").

In FIG. 23, the reference symbols 101a, 101b denote flue walls between which a gas to be measured flows. A light-emitting unit flange 201a and a light-receiving unit flange 201b are respectively disposed, opposing each other, on the flue walls 101a, 101b.

A light-emitting unit housing 203a is attached to the light-emitting unit flange 201a via a mounting bracket 202a. Optical components such as a laser light source 204, a collimating lens 205 or the like, are built into the light-emitting unit housing 203a. A light-receiving unit housing 203b is attached to the light-receiving unit flange 201b via a mounting bracket 202b. A lens 206, a light-receiving element 207, and a light-receiving unit circuit board 208 that processes output signals of the light-receiving element 207 are built into the light-receiving unit housing 203b.

In the above configuration, laser light emitted by the laser light source 204 is irradiated into the flue interior, as the space to be measured, and is received by the light-receiving element 207 inside the light-receiving unit housing 203b that is disposed opposing the laser light source 204.

In such light reception, laser light becomes absorbed when gas to be measured is present in the flue interior. Therefore, a light reception signal processing circuit on the light-receiving unit circuit board 208 calculates the concentration of the gas to be measured by relying on the correspondence between optical absorption and the concentration of the gas to be measured.

Patent literature 1: Japanese Patent Application Publication No. H07-151681 (Title of the invention "Gas Concentration Measurement Device", for instance paragraphs [0004], [0030]; FIG. 7 and FIG. 8)

Patent literature 2: Japanese Patent Application Publication No. 2009-47677 (Title of the invention "Laser-Type Gas Analyzer", for instance, paragraphs [0029]-[0038]; FIG. 1 to FIG. 7)

Regulations concerning marine exhaust gas have become stricter in recent years. Regulations on SOx, specifically, require that the criteria of Expression 1 below be met by a measured concentration of $SO_2$ gas and $CO_2$ gas in exhaust gas.

$$SO_2 \text{ gas concentration (ppm)} + CO_2 \text{ gas concentration (vol \%)} < 4.3 \qquad [\text{Math. 1}]$$

A laser-type gas analyzer such as the above-described one can be used as a means for measuring the concentration of $SO_2$ gas and $CO_2$ gas. However, most conventional laser-type gas analyzers can measure one type of gas to be measured per device, while laser-type gas analyzers that can detect the concentration of two or more types of gas, for instance $CO+CO_2$, $NH_3+H_2O$, $HCl+H_2O$, or the like, are limited as regards the types of gas. Two laser-type gas analyzers have been conventionally necessary to measure the concentration of $SO_2$ gas and $CO_2$ gas, as in marine exhaust gas.

The reasons for this are explained next.

The optical absorption spectrum of the $SO_2$ gas lies in the mid-infrared region. For instance, FIG. 24 is the optical absorption spectrum of $SO_2$. A quantum cascade laser or the like that emits laser light of a wavelength of a mid-infrared region can be conceivably used, as the laser light source, in order to detect such an optical absorption spectrum.

The optical absorption spectrum of $CO_2$ gas is in the near-infrared region. For instance, FIG. 25 is the optical absorption spectrum of $CO_2$. A semiconductor laser or the like that emits laser light of a wavelength of a near-infrared region can be conceivably used, as the laser light source, in order to detect such an optical absorption spectrum.

Two laser-type gas analyzers having different laser light sources are thus required. The cost of the analyzers and construction costs increase as a result. This is compounded with the problem of the increased equipment size. Compact laser-type gas analyzers that measure the concentration of both $SO_2$ gas and $CO_2$ gas in a single device have become thus a necessity.

Marine exhaust gas comprises water and soot (dust). The influence of light amount attenuation by dust can be corrected by resorting to the conventional technology disclosed in Patent literature 2, such that the gas concentration can be accurately measured even if dust is hypothetically present in the flue.

For instance, a wavelength range scannable by the near-infrared laser element that is used encompasses light of a wavelength that is unaffected by absorption by $CO_2$ gas having a spectrum such as the one illustrated in FIG. 25. By resorting to the conventional technique of Patent literature 2, therefore, the gas concentration can be measured accurately by correcting the received light amount using light of a wavelength that is unaffected by absorption by a gas component to be measured.

In $SO_2$ gas having a spectrum such as the one illustrated in FIG. 26, however, the wavelength range that can be emitted by the mid-infrared laser element that is used does not include light of a wavelength unaffected by absorption by $SO_2$ gas. Accordingly, DC-type absorption occurs due to the gas to be measured. This was problematic in that, with a light amount decrease due to dust being of DC type, it was difficult to discriminate between absorption by the gas to be measured and light amount attenuation by dust, and to measure accurately gas concentrations by correcting received light amounts, when measuring a gas such as $SO_2$ gas.

Further problems arise when water is present in the exhaust gas in a substantial amount. The optical absorption spectrum of water appears at multiple sites outside the optical absorption spectrum of $SO_2$ gas, as the gas to be measured, in the mid-infrared region (FIG. 24) for measuring $SO_2$ gas. FIG. 27 illustrates the optical absorption spectrum of water. The optical absorption spectrum of water lies in the mid-infrared region, as does that of $SO_2$ gas. It is therefore very difficult to measure $SO_2$ gas concentration by excluding the optical absorption spectrum of water.

Specifically, when the concentration of water in the space to be measured is high, the laser light that is emitted by the quantum cascade laser, as a laser light source, is affected also by water, besides the gas to be measured.

This is problematic in that the received light amount is attenuated due to such an influence. This feature will be explained next. FIG. 28 illustrates the levels of a light reception signal (in other words, received light amount) of instances of experimental assessment of the influence of absorption by water upon detection of $SO_2$ gas with the optical absorption spectrum wavelength of $SO_2$ gas set to about 7.2 μm.

If attenuation of the received light amount arises only as a result of the influence of dust, such attenuation can be corrected by resorting to the method disclosed in Patent literature 2. However, FIG. 28 reveals that that the received light amount becomes increasingly attenuated as the water concentration (volume concentration) rises. As a result, a problem arises thus in a conventional laser-type gas analyzer in that when water is present in the space to be measured, the measured value of the gas to be measured becomes attenuated, and the gas concentration cannot be measured accurately.

It has become thus necessary to nullify both the influence of dust and the influence of water in order to analyze the $SO_2$ gas concentration and the $CO_2$ gas concentration in marine exhaust gas.

Similar problems arise when measuring the gas concentration of a first gas to be measured in a mid-infrared region, such as $SO_2$ gas, and the gas concentration of a second gas to be measured in a near-infrared region, such as $CO_2$ gas. As a result, it has been necessary to remove the influence of dust and/or the influence of water.

SUMMARY OF THE INVENTION

The goal to be attained by the present invention, therefore, is to provide a laser-type gas analyzer that can measure, with high precision and using one single device, the gas concentration of a first gas to be measured in a mid-infrared region, and the gas concentration of a second gas to be measured in a near-infrared region, even in a measurement environment where dust and water at a high concentration are present.

To attain the above goal, a first aspect of the invention includes:

a mid-infrared laser light-emitting unit that emits laser light of a wavelength band of a mid-infrared region that includes an optical absorption spectrum of a first gas to be measured;

a mid-infrared laser driving unit that drives the mid-infrared laser light-emitting unit;

a mid-infrared laser optical unit that collimates the laser light emitted by the mid-infrared laser light-emitting unit, and irradiates the light into a space to be measured in which the first gas to be measured is present;

a mid-infrared light-receiving unit that receives the laser light irradiated by the mid-infrared laser optical unit, and outputs the received laser light as an electrical mid-infrared light reception signal;

a mid-infrared light reception signal processing and computing unit that extracts, from the mid-infrared light reception signal, a signal component affected by optical absorption by the first gas to be measured, and calculates a gas concentration of the first gas to be measured on the basis of an amount of change of this signal component;

a near-infrared laser light-emitting unit that emits, at respective times, first laser light of a wavelength band of a near-infrared region that includes an optical absorption spectrum of a second gas to be measured, second laser light of a wavelength band of a near-infrared region that includes an optical absorption spectrum of water, and third laser light of a wavelength band of a near-infrared region in which the optical absorption spectra of water, the first gas to be measured and the second gas to be measured are equal to or smaller than a predetermined amount;

a near-infrared laser driving unit that drives the near-infrared laser light-emitting unit;

a near-infrared laser optical unit that collimates, at respective times, the first, second and third laser light emitted by the near-infrared laser light-emitting unit, and irradiates the collimated light to the space to be measured;

a near-infrared light-receiving unit that receives, at respective times, the first, second and third laser light irradiated by the near-infrared laser optical unit, and outputs the received light as respective electrical near-infrared light reception signals;

a near-infrared light reception signal processing and computing unit that performs, at respective times, processes of extracting, from the near-infrared light reception signal of the first laser light, a signal component affected by optical absorption by the second gas to be measured, and computing a gas concentration of the second gas to be measured on the basis of an amount of change of this signal component, computing a water concentration in the space on the basis of the near-infrared light reception signal of the second laser light, and computing a light amount decrement due to dust on the basis of the near-infrared light reception signal of the third laser light; and a gas concentration correcting unit that corrects the gas concentration of the first gas to be measured, as worked out by the mid-infrared light reception signal processing and computing unit and the gas concentration of the second gas to be measured, as worked out by the near-infrared light reception signal processing and computing unit, in use of the water concentration and light amount decrement as worked out by the near-infrared light reception signal processing and computing unit.

A second aspect of the invention includes a laser-type gas analyzer, wherein the first gas to be measured is $SO_2$ gas and the second gas to be measured is $CO_2$ gas.

A third aspect of the invention is a laser-type gas analyzer, wherein the wavelength of laser light of the mid-infrared region emitted by the mid-infrared laser light-emitting unit ranges from 3 to 10 μm, and the wavelength of the laser light of the near-infrared region emitted by the near-infrared laser light-emitting unit ranges from 0.7 to 3 μm.

The present invention succeeds in providing a laser-type gas analyzer that can measure, with high precision and using one single device, the gas concentration of a first gas to be measured in a mid-infrared region, and the gas concentration of a second gas to be measured in a near-infrared region, even in a measurement environment where dust and water at a high concentration are present.

BRIEF DESCRIPTION OF THE DRAWINGS

FIG. 4A is a characteristic diagram illustrating the relationship between emission wavelength and current in a laser element, and FIG. 4B is a characteristic diagram illustrating the relationship between emission wavelength and temperature in a laser element;

DETAILED DESCRIPTION

Embodiments of the present invention will be explained next with reference to accompanying drawings. As a specific example, the laser-type gas analyzer in the embodiments is a device that analyzes $SO_2$ gas concentration and $CO_2$ gas concentration in marine exhaust gas, wherein a first gas to be measured is $SO_2$ gas, and a second gas to be measured is $CO_2$ gas. The laser-type gas analyzer can measure $SO_2$ gas concentration using a mid-infrared laser light-emitting unit and can measure $CO_2$ gas concentration using a near-infrared laser light-emitting unit, while nullifying the influence of water present in the space to be measured and the influence of dust present in the space to be measured, in an environment where dust and water at a high concentration are present, such as marine exhaust gas. The laser-type gas analyzer measures thus, with high precision, the targeted gas concentrations.

Figure 1:
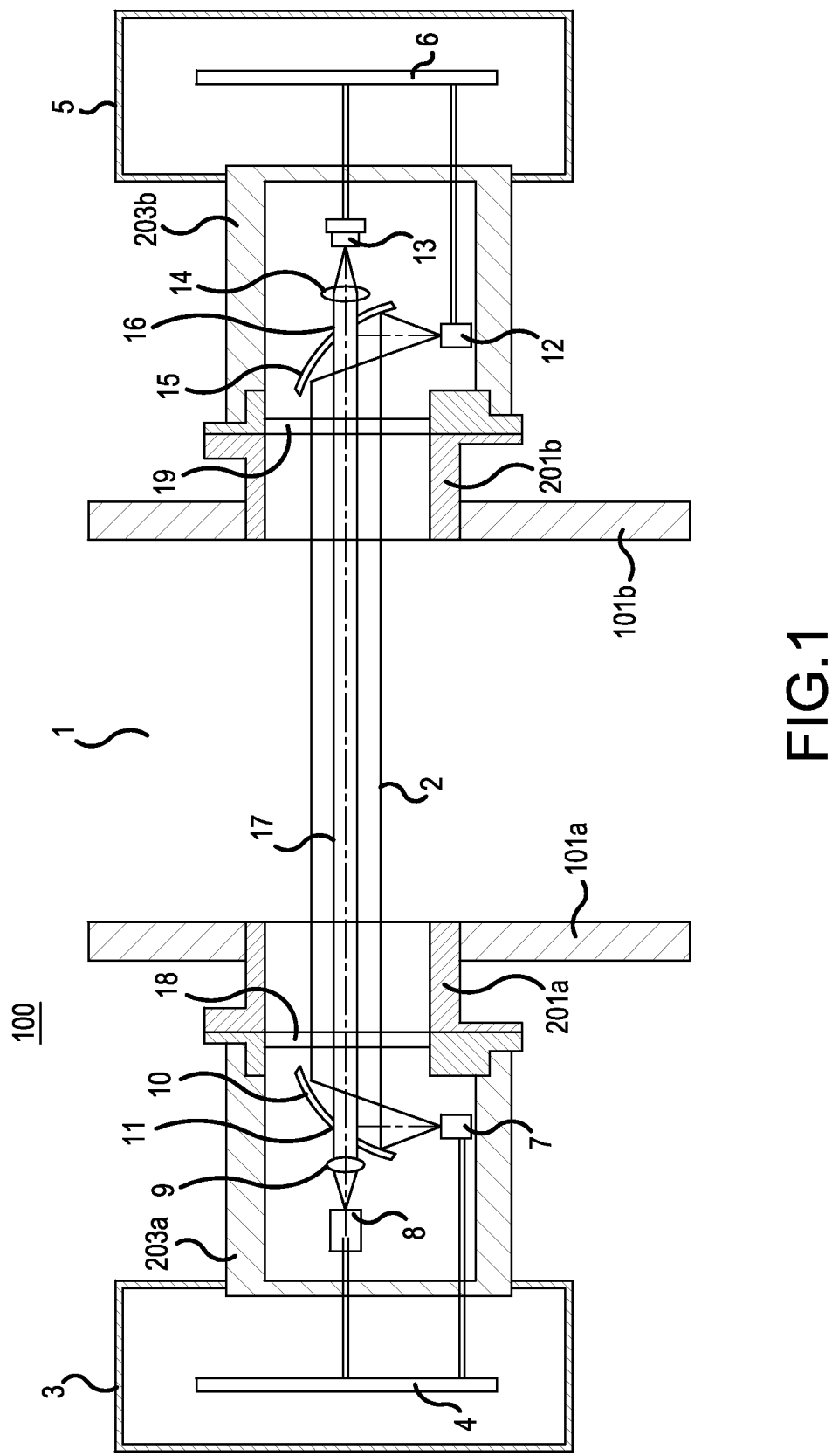
FIG. 1 is a configuration diagram of a laser-type gas analyzer according to an embodiment of the present invention.

Firstly, FIG. 1 illustrates the overall configuration of a laser-type gas analyzer according to an embodiment. In FIG. 1, a light-emitting unit flange 201a and a light-receiving unit flange 201b are respectively fixed, by welding or the like, for instance to flue walls 101a, 101b of a flue through the interior whereof a gas to be measured flows.

A light-emitting unit housing 203a is attached to the light-emitting unit flange 201a, and a light-emitting unit case 3 is attached to the light-emitting unit housing 203a. A mid-infrared laser light-emitting unit 7 that emits mid-infrared laser light, a near-infrared laser light-emitting unit 8 that emits near-infrared laser light, a lens 9 and a concave mirror 10 are hermetically disposed inside the light-emitting unit housing 203a. A window 18 that is transmissive to light of the used wavelength, is also provided, to secure thereby the airtightness inside the light-emitting unit housing 203a.

Figure 2:
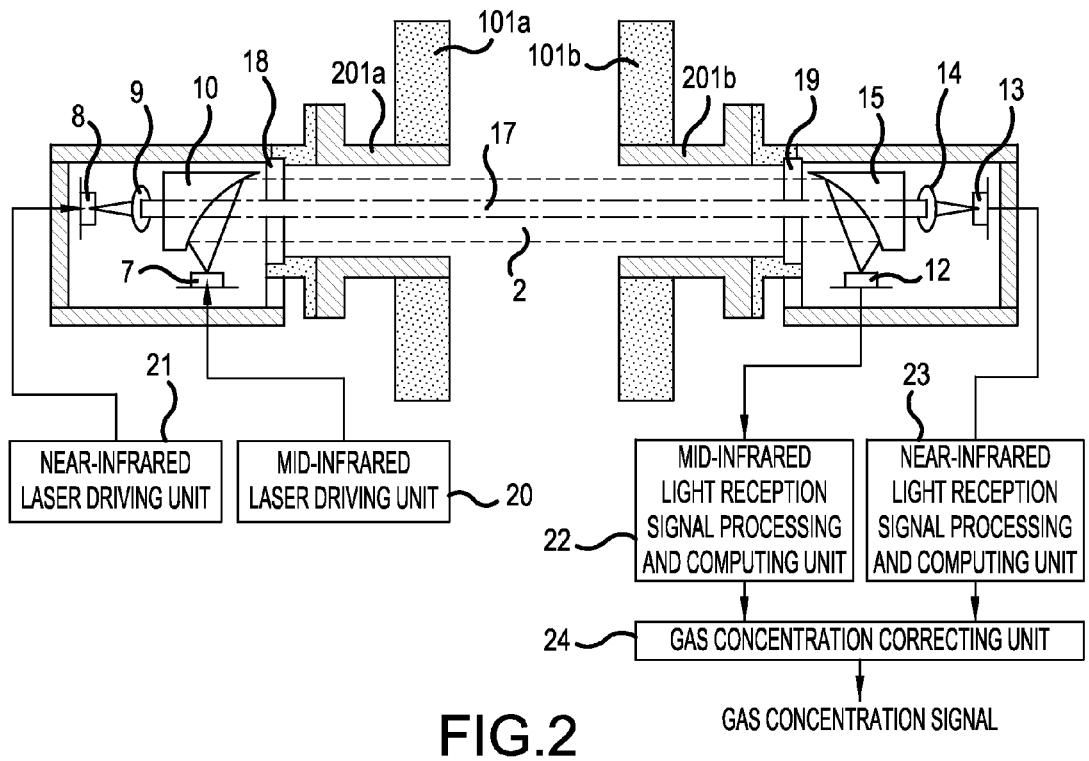
FIG. 2 is a circuit block diagram of a laser-type gas analyzer according to an embodiment of the present invention.

The light-emitting unit case 3 is attached to the light-emitting unit housing 203a, and a mid-infrared laser driving unit 20 and a near-infrared laser driving unit 21 are installed on a light-emitting unit circuit board 4 inside the light-emitting unit case 3, as illustrated in detail in the block diagram of FIG. 2. Electric signals are sent by the mid-infrared laser driving unit 20 and the near-infrared laser driving unit 21 to the mid-infrared laser light-emitting unit 7 and the near-infrared laser light-emitting unit 8. The mid-infrared laser light-emitting unit 7 is configured to emit mid-infrared laser and the near-infrared laser light-emitting unit 8 is configured to emit near-infrared laser.

The mid-infrared laser light-emitting unit 7 is, for instance, an element such as a quantum cascade laser that emits mid-infrared laser light having a wavelength ranging from 3 to 10 μm in the mid-infrared region, including the optical absorption spectrum of $SO_2$ gas being the first gas to be measured. A laser drive signal such that the wavelengths in the above mid-infrared region are swept is generated in the mid-infrared laser driving unit 20, to prompt emission in the mid-infrared laser light-emitting unit 7.

The near-infrared laser light-emitting unit 8 is a laser element that emits near-infrared laser light having a wavelength ranging from 1.5 to 2.1 μm in a near-infrared region that includes the optical absorption spectrum of $CO_2$ gas, which is a second gas to be measured. A laser drive signal such that the wavelengths in the above near-infrared region are swept is generated in the near-infrared laser driving unit 21, to prompt emission in the near-infrared laser light-emitting unit 8.

The light emitted by the mid-infrared laser light-emitting unit 7 is made into parallel light through collimation at the concave mirror 10, as a mid-infrared laser optical unit of the present invention, passes through the center of the light-emitting unit flange 201a, and is irradiated into the flue interior 1 as mid-infrared laser light 2. The mid-infrared laser light 2 is affected by optical absorption by $SO_2$ gas, which is the first gas to be measured that is present in the flue interior 1. The mid-infrared laser light 2 is also affected by light scattering due to dust that is present concurrently. The mid-infrared laser light 2 is particularly affected by water in the mid-infrared region.

The light emitted by the near-infrared laser light-emitting unit 8 is made into parallel light by the lens 9, and passes then, as near-infrared laser light 17, through the center of the light-emitting unit flange 201a, through an aperture 11 that is formed near the center of the concave mirror 10, and is irradiated into the flue interior 1. The lens 9 and the aperture 11 make up the near-infrared laser optical unit of the present invention. As described above, the near-infrared laser light 17 is emitted coaxially within the mid-infrared laser light 2. The near-infrared laser light 17 is affected by optical absorption from $CO_2$ gas, which is the second gas to be measured in the flue interior 1. The near-infrared laser light 17 is also affected by light scattering due to dust that is present concurrently. There are wavelengths in the near-infrared region that are not affected by water, and one such wavelength is used herein.

A light-receiving unit housing 203b is attached to the light-receiving unit flange 201b. The mid-infrared laser light 2 that passes through the flue interior 1 is condensed by a concave mirror 15 disposed hermetically inside the light-receiving unit housing 203b, and is received by a mid-infrared light-receiving element 12. A window 19 that is transmissive to light of the used wavelength is also disposed, to secure thereby the airtightness inside the light-receiving unit housing 203b. The concave mirror 15 and the mid-infrared light-receiving element 12 make up the mid-infrared light-receiving unit of the present invention.

The mid-infrared light-receiving element 12 is for instance an MCT (Mercury Cadmium Tellurium) photoconductive element that is sensitive to wavelengths in the mid-infrared region. An output signal of the mid-infrared light-receiving element 12 is inputted to a mid-infrared light reception signal processing and computing unit 22 that is installed on a light-receiving unit circuit board 6 inside the light-receiving unit case 5 (see FIG. 2). The mid-infrared light reception signal processing and computing unit 22 performs signal processing on a mid-infrared light reception signal from the mid-infrared light light-receiving element 12, such that a signal change component by optical absorption from $SO_2$ gas is extracted and obtained in the form of a gas concentration signal of $SO_2$ gas. The mid-infrared light reception signal processing and computing unit 22 measures the concentration of $SO_2$ gas uncorrected for the influence of water or for light amount attenuation.

The near-infrared laser light 17 passes through an aperture 16 that is formed near the center of the concave mirror 15, is condensed by a lens 14, and is received by a near-infrared light-receiving element 13. The aperture 16, the lens 14 and the near-infrared light-receiving element 13 make up the near-infrared light-receiving unit of the present invention.

The near-infrared light-receiving element 13 is an element, such as a photodiode, having sensitivity towards wavelengths in the near-infrared region. An output signal of the near-infrared light-receiving element 13 is inputted to a near-infrared light reception signal processing and computing unit 23 (see FIG. 2) of the light-receiving unit circuit board 6. The near-infrared light reception signal processing and computing unit 23 performs signal processing on a signal from the near-infrared light light-receiving element 13, to measure as a result the concentration of $CO_2$ gas and the concentration of water, uncorrected light amount attenuation, and to measure the light amount decrease due to scattering upon collision of the light with dust.

The mid-infrared light reception signal processing and computing unit 22 and the near-infrared light reception signal processing and computing unit 23 are connected to a gas concentration correcting unit 24. Through correction in the latter, accurate gas concentrations are calculated in which water concentration and the light amount decrease derived from dust have been factored in.

The operation of the various units will be explained next. The various units of the mid-infrared light reception signal processing system that measures the first gas to be measured will be explained first. As illustrated in more detail in FIG. 3, the mid-infrared laser driving unit 20 further comprises a wavelength scanning drive signal generating unit 20a, a high-frequency modulated signal generating unit 20b, a laser drive signal generating unit 20c, and a temperature control unit 20d. The mid-infrared laser light-emitting unit 7 further comprises a mid-infrared laser element 7a, a temperature detecting unit (thermistor) 7b, and a temperature regulating unit (Peltier element) 7c.

Figure 4A:
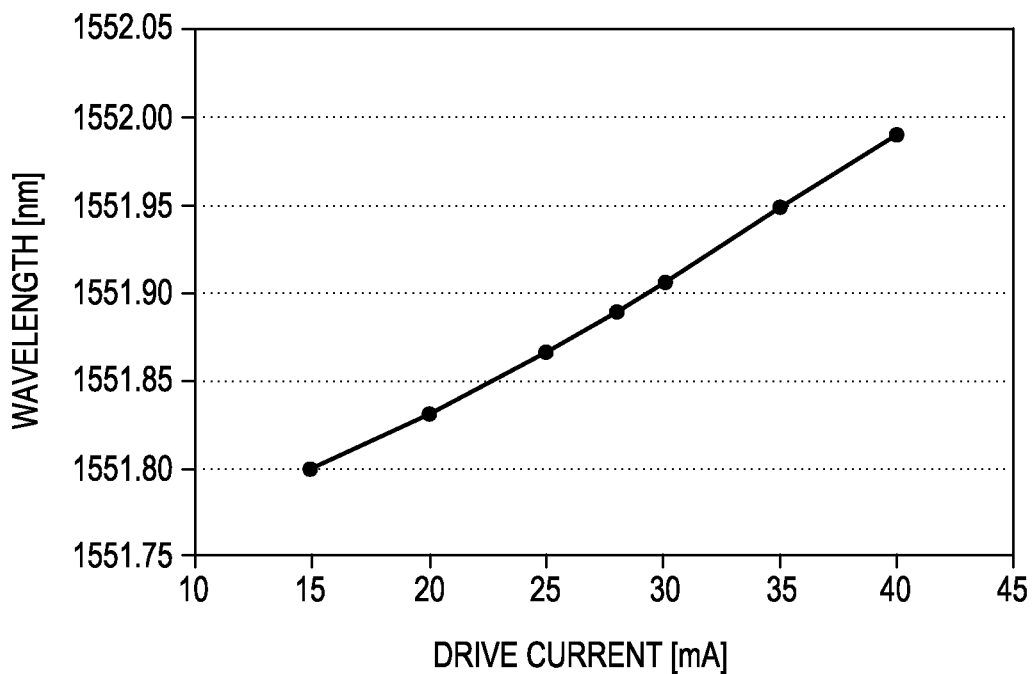
FIGS. 4A and 4B are a set of explanatory diagrams of emission wavelength, where
Figure 4B:
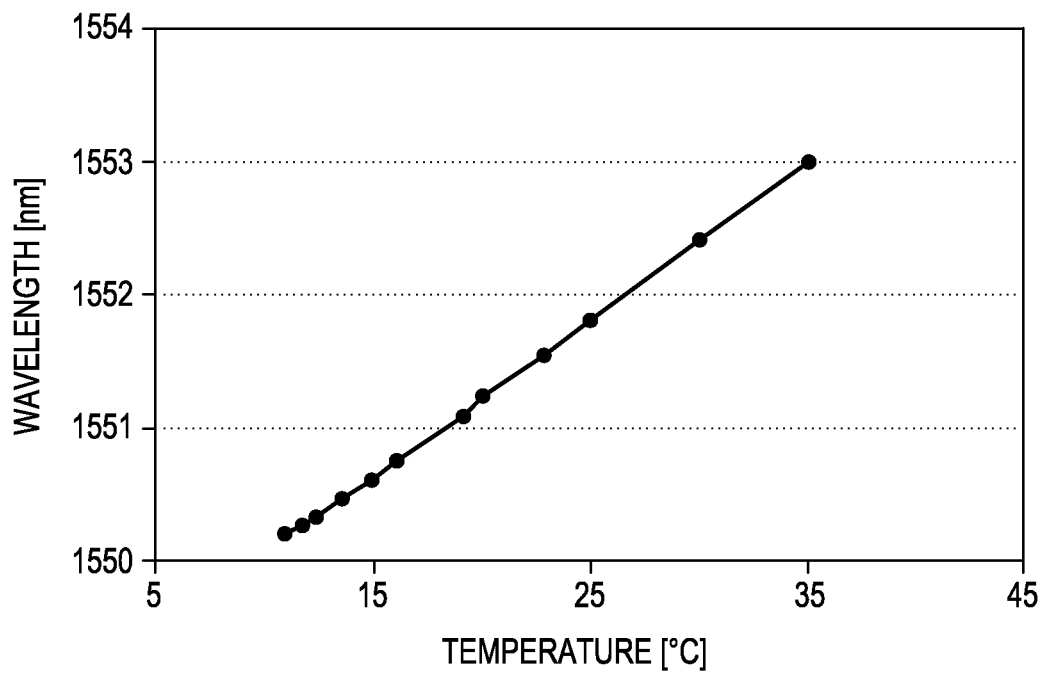

The mid-infrared laser element 7a can emit light at a wavelength, and a surrounding wavelength region, for which the emission wavelength matches the absorption characteristic of the first gas to be measured. Further, the mid-infrared laser element 7a can modify the emission wavelength on the basis of drive current, as illustrated in FIG. 4a, and can modify the emission wavelength on the basis of the temperature, as illustrated in FIG. 4B. In this embodiment, sulfur dioxide gas ($SO_2$ gas) is measured as the first gas to be measured, and the wavelengths that are used are absorption wavelengths of sulfur dioxide gas ($SO_2$ gas).

Figure 3:
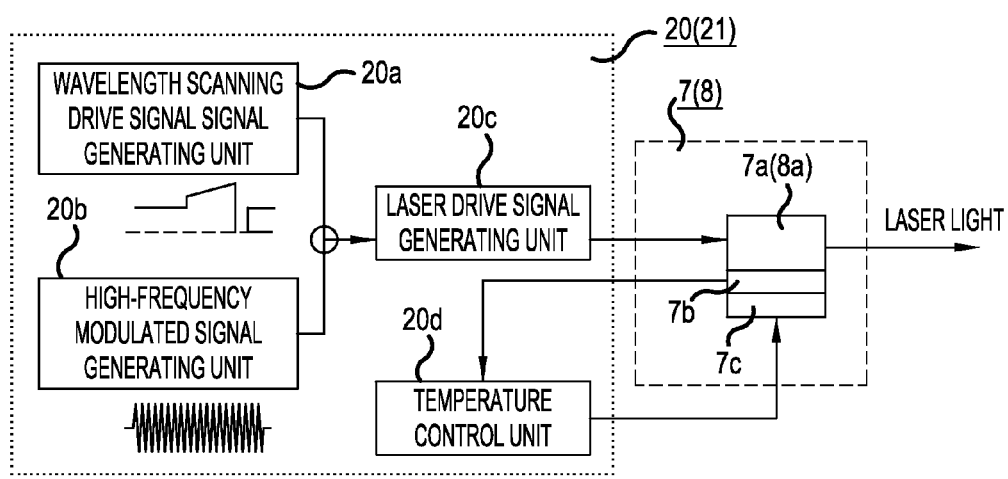
FIG. 3 is a circuit block diagram of a laser light-emitting unit and a laser driving unit.

In FIG. 3, the temperature of the mid-infrared laser element 7a is detected by the temperature detecting unit 7b such as a thermistor or the like. The temperature detecting unit 7b is connected to the temperature control unit 20d of the mid-infrared laser driving unit 20. In order to stabilize the emission wavelength of the mid-infrared laser element 7a and to regulate the wavelength thereof, the temperature control unit 20d controls the temperature of the temperature regulating unit 7c, such as a Peltier element, by PID control or the like, to regulate the temperature of the mid-infrared laser element 7a, in such a manner that a resistance value obtained from the temperature detecting unit 7b, such as a thermistor or the like, takes on a constant value.

Upon input, to the laser drive signal generating unit 20c, of the output signal from the wavelength scanning drive signal generating unit 20a that modifies the emission wavelength of laser in such a way so as to scan the absorption wavelengths of $SO_2$ gas, and of the output signal of the high-frequency modulated signal generating unit 20b for frequency modulation of the emission wavelength, for instance with a sine wave of about 10 kHz, for detection of the absorption waveform of $SO_2$ gas, the laser drive signal generating unit 20c combines these output signals to generate thereby a drive signal, performs V-I conversion on this drive signal, and supplies the drive signal to the mid-infrared laser element 7a.

Figure 5:
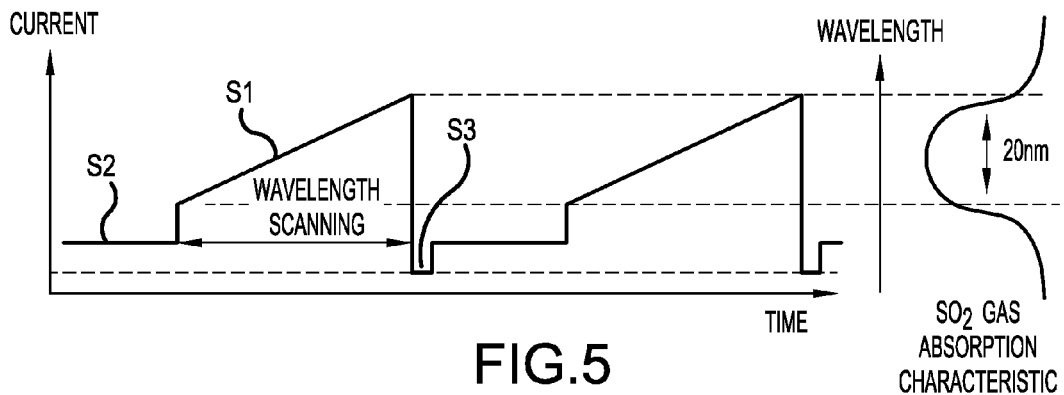
FIG. 5 is a diagram illustrating a wavelength scanning drive signal.

Modulation of laser light will be explained next. FIG. 5 illustrates an output signal of the wavelength scanning drive signal generating unit 20a. A wavelength scanning drive signal $S_1$ for scanning the absorption characteristic of $SO_2$ gas causes the drive current value of the mid-infrared laser element 7a to vary linearly, whereby the emission wavelength of the mid-infrared laser element 7a is caused to vary gradually, to scan for instance an absorption characteristic of about 20 nm. The purpose of a signal $S_2$ is to keep the drive current value at or above a threshold value at which the mid-infrared laser element 7a is stable, and to elicit emission at a constant wavelength. Further, the drive current value is set to 0 mA with a signal $S_3$.

A waveform diagram of the modulated signal that is outputted by the high-frequency modulated signal generating unit 20b is depicted below the high-frequency modulated signal generating unit 20b in FIG. 3. This modulated signal is a sine wave having for instance a frequency of 10 kHz and a wavelength width of about 0.2 nm.

Figure 6:
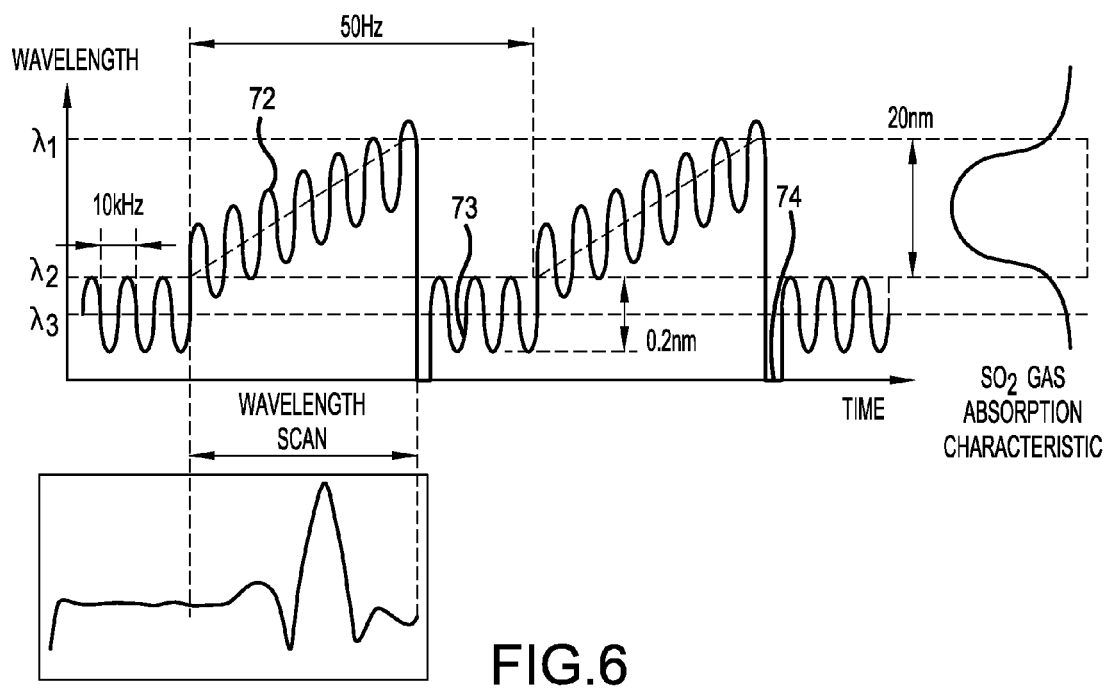
FIG. 6 is a diagram illustrating a drive signal for a laser element.

FIG. 6 is a waveform diagram of a drive signal outputted by the laser drive signal generating unit 20c of FIG. 3 (composite signal of the output signal of the wavelength scanning drive signal generating unit 20a and the output signal of the high-frequency modulated signal generating unit 20b). This drive signal has a trapezoid shape that is repeated at constant cycles. When the laser drive signal generating unit 20c supplies this drive signal to the mid-infrared laser element 7a, modulated light that allows detecting, with a wavelength width of about 0.2 nm, an absorption characteristic of about 20 nm of the gas to be measured, is emitted by the mid-infrared laser element 7a.

Frequency-modulated laser light of a predetermined wavelength, for scanning the absorption characteristic of $SO_2$ gas, is emitted as a result by the mid-infrared laser element 7a. As illustrated in FIG. 1, the laser light emitted by the mid-infrared laser element 7a is emitted as parallel mid-infrared laser light 2, by the concave mirror 10. The temperature of the mid-infrared laser element 7a is adjusted beforehand in such a manner that $SO_2$ gas is measured at the central portion of the wavelength scanning drive signal.

Such mid-infrared laser light 2 propagates through the flue interior, being the interior zone between the flue walls 101a, 101b (space through which the gas to be measured flows), and is absorbed by $SO_2$ gas as the laser light passes through this space. The operation and function of the mid-infrared laser driving unit, mid-infrared laser light-emitting unit and mid-infrared laser optical unit of the present invention are thus as described above.

The mid-infrared light-receiving unit of the present invention will be explained next.

Detection light having propagated through a space in which $SO_2$ gas, $CO_2$ gas, water and dust are present, and having undergone absorption by $SO_2$ gas, among the foregoing, is condensed by the concave mirror 15, and is thereafter received by the mid-infrared light-receiving element 12. The mid-infrared light-receiving element 12 outputs a detection signal, in the form of an electric signal, in response to the received light amount. The mid-infrared light-receiving element 12 is for instance a photodiode. An element is used herein that has sensitivity towards the laser emission wavelength.

Figure 7:
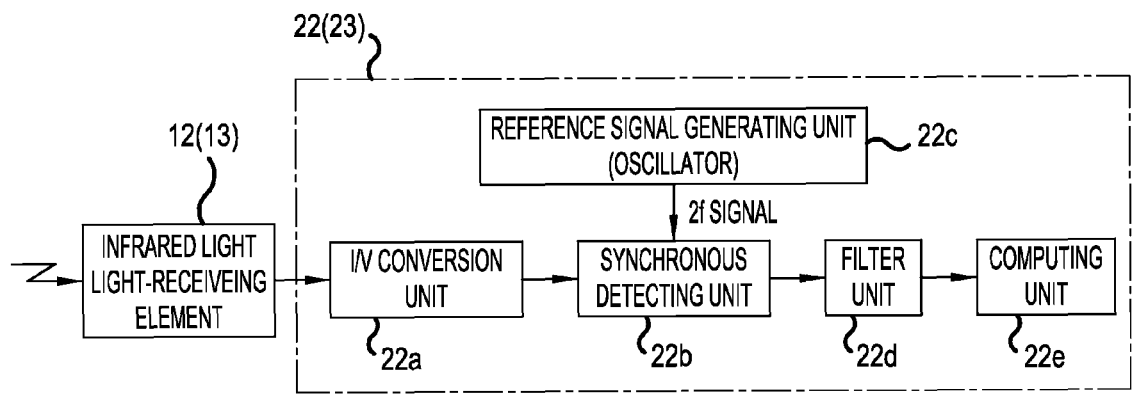
FIG. 7 is a block diagram of a mid-infrared light reception signal processing and computing unit and a near-infrared light reception signal processing and computing unit.

The mid-infrared light reception signal processing and computing unit 22 will be explained next. As illustrated in FIG. 7, the mid-infrared light reception signal processing and computing unit 22 comprises an I/V conversion unit 22a, a synchronous detecting unit 22b, a reference signal generating unit (oscillator) 22c, a filter unit 22d and a computing unit 22e. The detection signal inputted from the mid-infrared light-receiving element 12 to the gas concentration computing unit 22 is converted from a current signal to a voltage signal by the I/V conversion unit 22a. The voltage signal has an output waveform such as the one illustrated in FIG. 9. This voltage signal is inputted to the synchronous detecting unit 22b. The reference signal generating unit (oscillator) 22c outputs, to the synchronous detecting unit 22b, a reference signal in the form of a double frequency signal of the high-frequency modulated signal by the high-frequency modulated signal generating unit 20b (FIG. 3). Only the amplitude of the double frequency component of the modulated signal is extracted in the synchronous detecting unit 22b.

Figure 22:
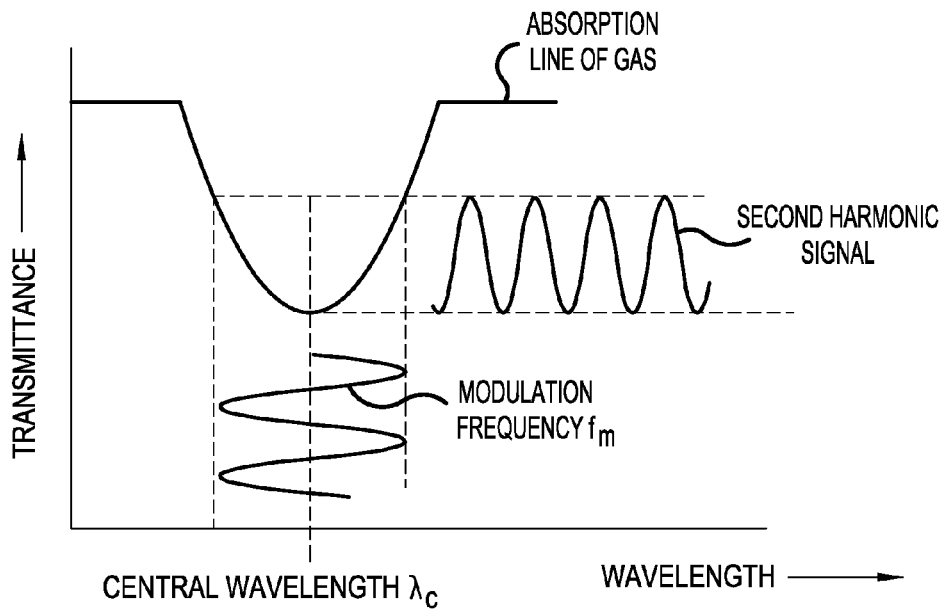
FIG. 22 is a diagram illustrating a concentration measurement principle according to a frequency modulation method.
Figure 23:
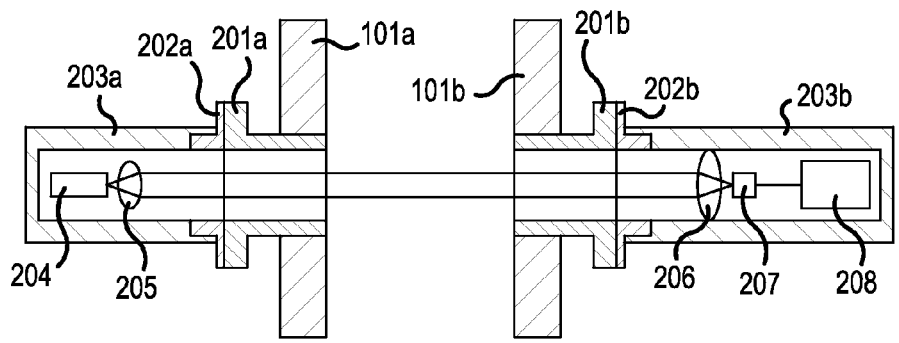
FIG. 23 is a configuration diagram of a conventional laser-type gas analyzer disclosed in Patent literature 2.
Figure 24:
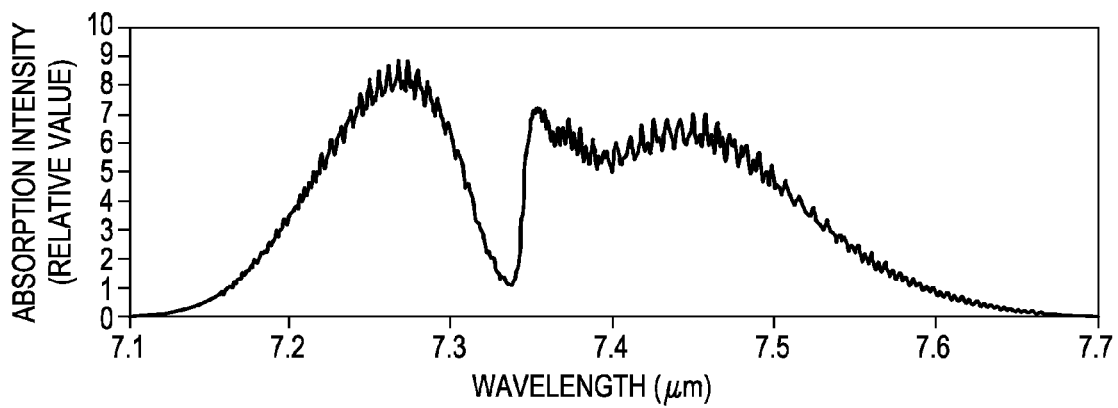
FIG. 24 is a diagram illustrating the optical absorption spectrum of sulfur dioxide ($SO_2$)

As illustrated in the concentration measurement principle according to a frequency modulation method in FIG. 22, explained above, the output of the mid-infrared laser element 7a is frequency-modulated at a central wavelength $\lambda_c$ with a modulation frequency $f_m$. Upon irradiation of the target $SO_2$ gas, the absorption lines of the gas behave substantially as a quadratic function with respect to frequency; therefore, the absorption lines fulfill the role of a discriminator, and a signal (second harmonic signal) of a frequency twice the modulation frequency $f_m$ is obtained in the light-receiving unit. This signal yields a value proportional to the $SO_2$ gas concentration. After noise removal at the filter unit 22d, the signal is inputted to the computing unit 22e, where the concentration of $SO_2$ gas is calculated.

An explanation follows next on a $SO_2$ gas concentration calculation according to a frequency modulation method. Upon absorption of light by $SO_2$ gas, a signal such as the one illustrated in FIG. 11 having passed through the filter unit 22d is outputted to the computing unit 22e. The computing unit 22e may calculate the peak amplitude and may integrate the signal change, since the peak value yields the gas concentration.

Figure 11:
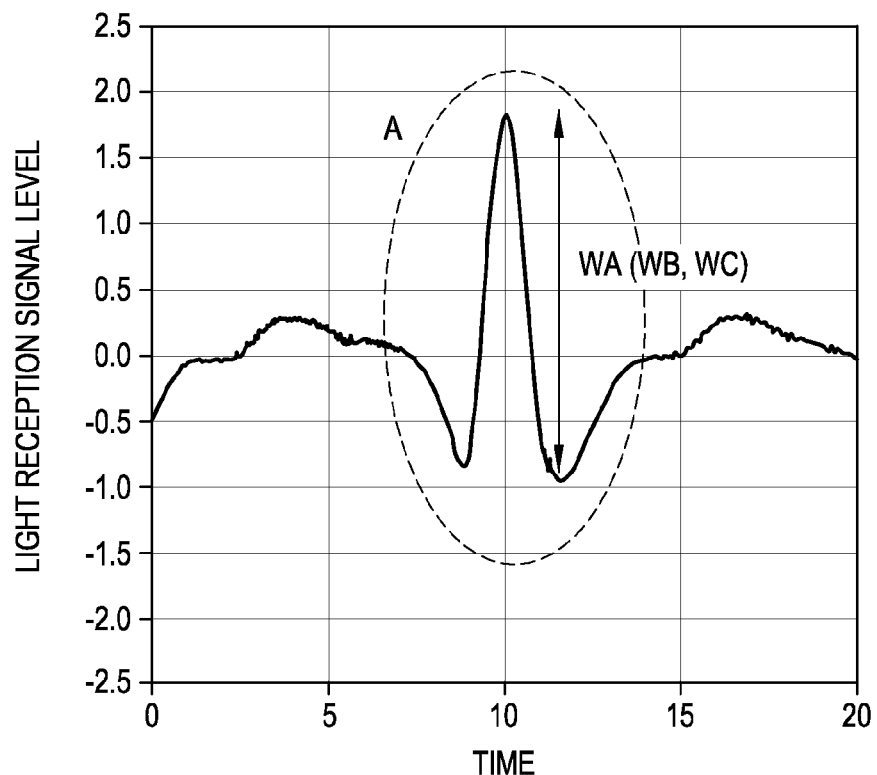
FIG. 11 is an output waveform diagram with absorption in a dust-free environment.

In one example, the computing unit 22e can detect the gas concentration by multiplying a peak amplitude $W_A$, such as the one illustrated in FIG. 11, by a given span calibration value $G_A$ for $SO_2$ gas concentration and a gas temperature correction coefficient $\alpha_A$.

$$\text{Concentration of } SO_2 \text{ gas} = \alpha_A \times G_A \times W_A \quad [\text{Math. 2}]$$

It suffices that the gas temperature correction coefficient $\alpha_A$ be a coefficient that is determined uniquely for the gas temperature of $SO_2$ gas. The form of the gas temperature correction coefficient $\alpha_A$ is not limited, and the latter may take a function form or a table form.

The $SO_2$ gas concentration must be corrected since it is affected by water and by light amount decrease due to dust. The computing unit 22e sends, to the gas concentration correcting unit 24, the $SO_2$ gas concentration as affected by water and by a light amount decrease due to dust. The process performed by the gas concentration correcting unit 24 will be explained further on. Detection of the $SO_2$ gas concentration by mid-infrared light is thus accomplished as described above.

Figure 8:
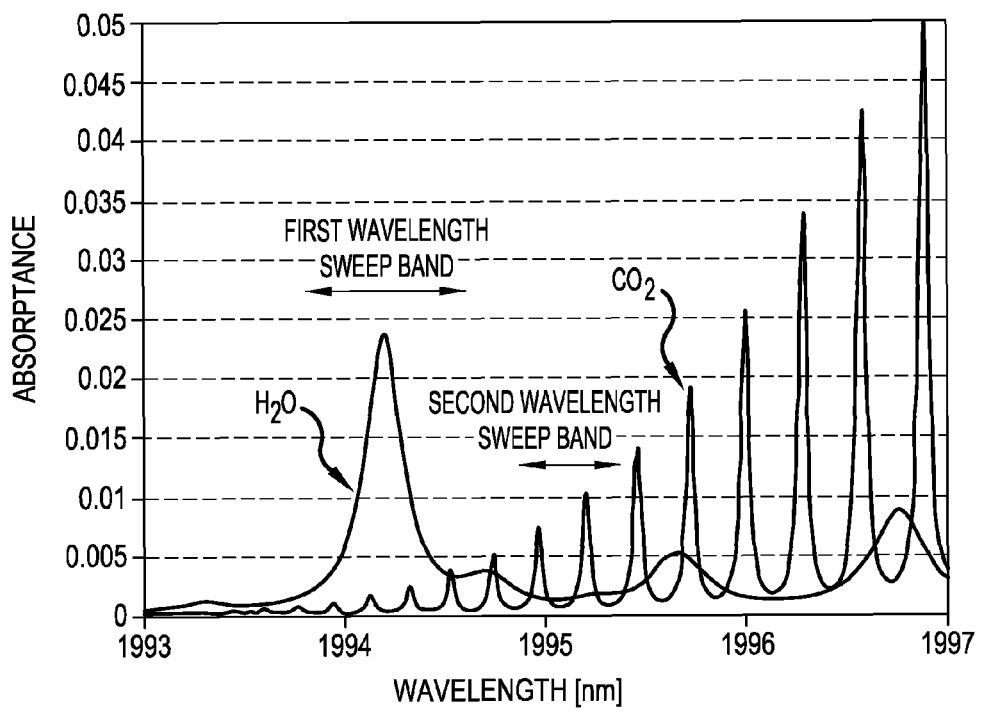
FIG. 8 is a diagram illustrating the optical absorption spectrum of $CO_2$ and water ($H_2O$) in the vicinity of the wavelength region 1.99 μm.

The near-infrared laser driving unit and a near-infrared light reception signal processing and computing unit will be explained next. The near-infrared laser driving unit 21 is driven so as to scan a first and a second wavelength sweep band, as illustrated in FIG. 8. As a first wavelength sweep band, there is firstly performed scanning for emission of laser light (second laser light of the present invention) such that the concentration of water is measured. As a second wavelength sweep band scanning is performed next for emission of laser light (first laser light of the present invention) such that gas concentration detection of the $CO_2$ gas, and subsequently, for emission of laser light (third laser light of the present invention) such that there is measured a light amount decrement. The first and second wavelength sweep bands succeed each other at respective separate times. For instance, the first wavelength sweep band is scanned over a predetermined period, and, subsequently, the second wavelength sweep band is scanned over a predetermined period.

Firstly, the near-infrared laser driving unit 21 scans the first wavelength sweep band (FIG. 8), i.e. performs scanning for emitting the second laser light of a wavelength band of the near-infrared region that includes the optical absorption spectrum of water but is free of optical absorption by $CO_2$ gas.

Figure 27:
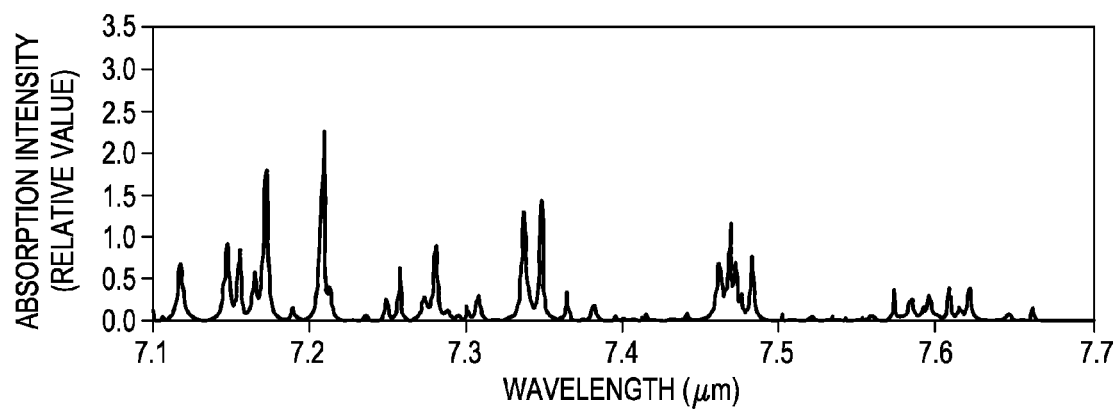
FIG. 27 is a diagram illustrating the optical absorption spectrum of water ($H_2O$) at a wavelength region from 7.1 to 7.7 μm.
Figure 28:
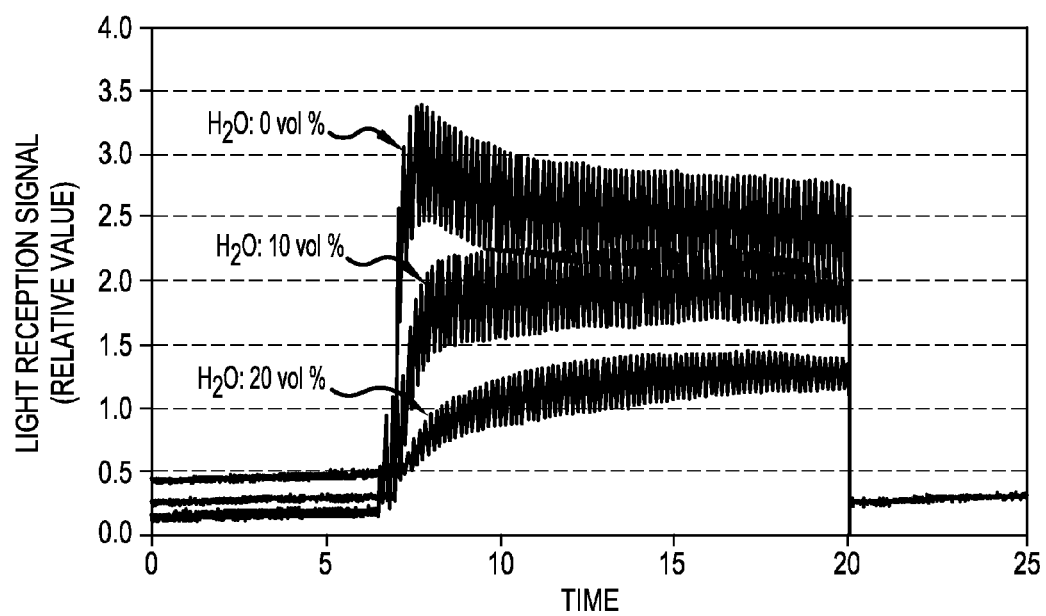
FIG. 28 is a diagram illustrating a light reception signal level affected by absorption by water, in the mid-infrared region.

The optical absorption spectrum of water is distributed widely over the mid-infrared region, as illustrated in FIG. 27. In a case where water is present in the space to be measured, it is difficult to measure accurately the $SO_2$ concentration, since optical absorption by $SO_2$ and optical absorption by water interfere with each other. In order to eliminate the influence of optical absorption by water, it would be conceivable to compare the optical absorption spectrum of water with the optical absorption spectrum of $SO_2$ gas, and to select, as much as possible, wavelengths at which the optical absorption spectrum of water is absent. Although this approach is workable up to a given degree of water concentration, optical absorption by water is very intense, and the gas concentration measurement value of $SO_2$ gas decreases for instance in a high-concentration environment where the water concentration is 10 vol % (volume concentration) or higher. The concentration of $SO_2$ gas cannot be measured with high precision as a result. In order to measure accurately the concentration of $SO_2$ gas, therefore, it is necessary to correct the concentration of $SO_2$ gas for the water concentration.

Besides the mid-infrared region, the optical absorption spectrum of water is present also in the near-infrared region. FIG. 8 illustrates optical absorption spectra of $CO_2$ and water in the vicinity of the wavelength 1.99 μm. By contrast, the optical absorption spectrum of $SO_2$ gas is absent in the near-infrared region up to 2 μm. Therefore, a semiconductor laser element is for instance selected that emits laser light in the vicinity of the wavelength 1.99 μm, as the near-infrared laser element 8 for measuring the concentration of $CO_2$ gas and the water concentration. Absorption lines of both $CO_2$ gas and water are both encompassed in the vicinity of the wavelength 1.99 μm. Thus, for instance, water can be measured in the first wavelength sweep region illustrated in FIG. 8, and $CO_2$ can be measured in the second wavelength sweep region.

The near-infrared laser driving unit 21 has the same configuration as the mid-infrared laser driving unit 20, and will be explained with reference to FIG. 3. As illustrated in FIG. 3, the near-infrared laser driving unit 21 of the present invention comprises the wavelength scanning drive signal generating unit 20a, the high-frequency modulated signal generating unit 20b, the laser drive signal generating unit 20c and the temperature control unit 20d. The near-infrared laser light-emitting unit 8 further comprises a near-infrared laser element 8a, the temperature detecting unit (thermistor) 7b, and the temperature regulating unit (Peltier element) 7c. The near-infrared laser optical unit comprises a lens 9 and an aperture 11.

The near-infrared laser element 8a can emit light at a wavelength, and a surrounding wavelength region, such that the emission wavelength matches the absorption characteristic of $CO_2$ gas (including absorption wavelengths of water and wavelengths at which there is virtually no absorption by $CO_2$ gas or water). Further, the near-infrared laser element 8a can modify the emission wavelength on the basis of drive current, and can modify the emission wavelength on the basis of temperature.

In FIG. 3, the temperature of the near-infrared laser element 8a is detected by the temperature detecting unit 7b such as a thermistor or the like. The temperature detecting unit 7b is connected to the temperature control unit 20d of the near-infrared laser driving unit 21. In order to stabilize the emission wavelength of the near-infrared laser element 8a and to regulate the wavelength thereof, the temperature control unit 20d controls the temperature of the temperature regulating unit 7c, such as a Peltier element or the like, by PID control or the like, to regulate the temperature of the near-infrared laser element 8a, in such a manner that a resistance value obtained from the temperature detecting unit 7b, such as a thermistor or the like, takes on a constant value.

Firstly, the near-infrared laser driving unit 21 scans the first wavelength sweep band for emitting the second laser light of a wavelength of a near-infrared region such that the region encompasses the optical absorption spectrum of water, but without optical absorption by $CO_2$ gas. Upon input, to the laser drive signal generating unit 20c, of the output signal from the wavelength scanning drive signal generating unit 20a that modifies the emission wavelength of laser in such a way so as to scan first wavelength sweep band, and of the output signal of the high-frequency modulated signal generating unit 20b for frequency modulation of the emission wavelength, for instance with a sine wave of about 20 kHz, for detection of an absorption waveform of water, the laser drive signal generating unit 20c combines these output signals to generate thereby a driving signal, performs V-I conversion on this driving signal, and supplies the resulting driving signal to the near-infrared laser element 8a.

Figure 13:
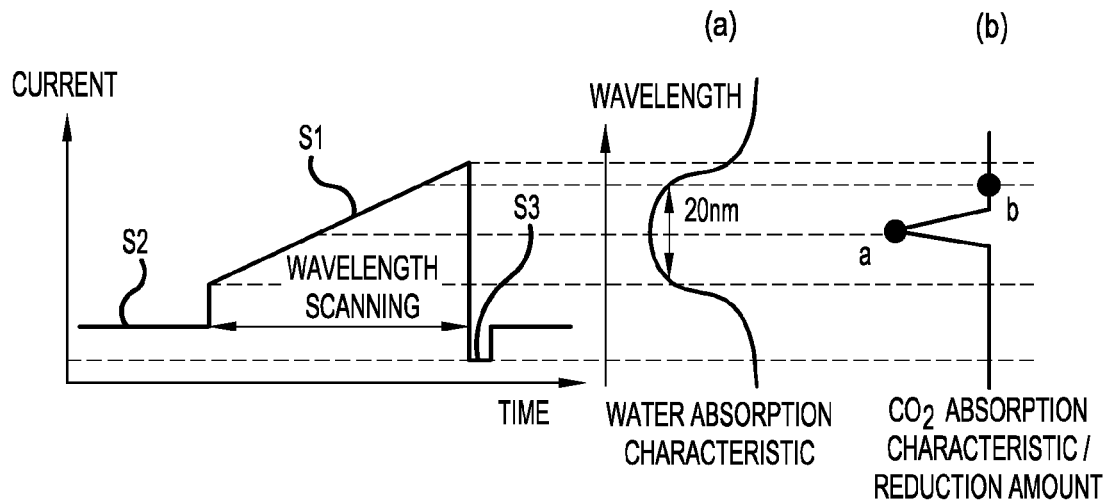
FIG. 13 is an explanatory diagram of a relationship between emission wavelength and detection wavelength in a laser element.

Modulation of the near-infrared laser light is identical to modulation of the mid-infrared light laser. Herein there is used the output signal of the wavelength scanning drive signal generating unit 20a of FIG. 13. A waveform diagram of the modulated signal that is outputted by the high-frequency modulated signal generating unit 20b is depicted below the high-frequency modulated signal generating unit 20b in FIG. 3. This modulated signal is a sine wave having for instance a frequency of 20 kHz and a wavelength width of about 0.2 nm. Such an output signal is used herein.

When the drive signal outputted by the laser drive signal generating unit 20c (composite signal of the output signal of the wavelength scanning drive signal generating unit 20a and the output signal of the high-frequency modulated signal generating unit 20b) is supplied by the laser drive signal generating unit 20c to the near-infrared laser element 8a, the latter outputs modulated light that allows detecting, with a wavelength width of about 0.2 nm, an absorption characteristic of about 20 nm of water.

Frequency-modulated laser light of a predetermined wavelength, for scanning the absorption characteristic of water, is emitted as a result by the near-infrared laser element 8a. The wavelength of this laser light is set so as to scan the absorption spectrum of water, as illustrated in FIG. 13(a). The laser light emitted by the near-infrared laser element 8a passes through a central hole of the concave mirror 10, and is emitted in the form of parallel near-infrared laser light 17, as illustrated in FIG. 1. The temperature of the near-infrared laser element 8a is adjusted beforehand in such a manner that water is measured at the central portion of the wavelength scanning drive signal. Laser light of a wavelength of the near-infrared region that includes the optical absorption spectrum of water is emitted as a result. Such near-infrared laser light 17 propagates through the flue interior, being the interior zone between the flue walls 101a, 101b (space through which the gas to be measured flows), and is absorbed by water as the laser light passes through this space.

The near-infrared light-receiving unit of the present invention will be explained next.

Laser light of a wavelength of a near-infrared region that includes the optical absorption spectrum of water undergoes absorption, in the detection light having propagated through a space in which $SO_2$ gas, $CO_2$ gas, water and dust are present. This detection light passes through the aperture 16 of the concave mirror 15, is thereafter condensed by the lens 14, and is then received by the near-infrared light-receiving element 13. The near-infrared light-receiving element 13 outputs a detection signal, in the form of an electric signal, in response to the received light amount. The near-infrared light-receiving element 13 is for instance a photodiode. An element is used herein that has sensitivity towards the laser emission wavelength.

The near-infrared light reception signal processing and computing unit 23 will be explained next. The internal configuration of the near-infrared light reception signal processing and computing unit 23 is identical to that of the mid-infrared light reception signal processing and computing unit 22, and comprises the I/V conversion unit 22a, the synchronous detecting unit 22b, the oscillator 22c, the filter unit 22d and the computing unit 22e, as illustrated in FIG. 7.

In the case of absorption by water, the detection signal that is inputted from the near-infrared light-receiving element 13 to the near-infrared light reception signal processing and computing unit 23 is converted from a current signal to a voltage signal by the I/V conversion unit 22a. This voltage signal as well has an output waveform such as the one illustrated in FIG. 9. This voltage signal is inputted to the synchronous detecting unit 22b. The reference signal generating unit (oscillator) 22c outputs, to the synchronous detecting unit 22b, a reference signal in the form of a double frequency signal of the high-frequency modulated signal by the high-frequency modulated signal generating unit 20b (FIG. 3). Only the amplitude of the double frequency component of the modulated signal is extracted in the synchronous detecting unit 22b.

As illustrated in the concentration measurement principle according to a frequency modulation method in FIG. 22, explained above, the output of the near-infrared laser element 8a is frequency-modulated at a central wavelength $\lambda_c$ with a modulation frequency $f_m$. The absorption lines of the gas behave substantially as a quadratic function with respect to frequency, and hence the absorption lines fulfill the role of a discriminator, and a signal (second harmonic signal) of a frequency twice the modulation frequency $f_m$ is obtained in the light-receiving unit. This signal yields a value proportional to the water concentration. The output from the synchronous detecting unit 22b is subjected to noise removal in the filter unit 22d, after which there is extracted a peak value such as the one illustrated in FIG. 11.

This signal is inputted to the computing unit 22e, and the water concentration is calculated in the computing unit 22e. The computing unit 22e may calculate the peak amplitude and may integrate the signal change, since the peak value yields the gas concentration.

In one example, the computing unit 22e can detect the water concentration by multiplying an amplitude $W_B$ of a peak value such as the one illustrated in FIG. 11 by a given span calibration value $G_B$ for water concentration and by a temperature correction coefficient $\alpha_B$.

$$\text{Water concentration} = \alpha_B \times G_B \times W_B \qquad \text{[Math. 3]}$$

It suffices that the temperature correction coefficient $\alpha_B$ be a coefficient that is determined uniquely for the temperature of water. The form of the temperature correction coefficient $\alpha_B$ is not limited, and the latter may take a function form or a table form.

The water concentration is used for correction, and accordingly the computing unit 22e sends the water concentration to the gas concentration correcting unit 24. The process performed by the gas concentration correcting unit 24 will be explained further on.

The near-infrared laser driving unit 21 scans next the second wavelength band, i.e. performs scanning for emitting, at respective times, the first laser light of a wavelength band of a near-infrared region that includes the optical absorption spectrum of $CO_2$ gas, and the third laser light of a wavelength band of a near-infrared region that includes just a small portion, i.e. includes just a predetermined extent or less, of the optical absorption spectra of water, the first gas to be measured ($SO_2$ gas) and the second gas to be measured ($CO_2$ gas).

Among the foregoing, the concentration of $CO_2$ gas is detected by using the optical absorption of $CO_2$ gas in this first laser light, and the third laser light is used to calculate the light amount decrement by dust, using near-infrared light. The detection principle of the light amount decrement has been explained above. The received light amount decreases when laser light is blocked due to the influence of dust. When the received light amount decreases, the amplitude of the detected gas absorption waveform decreases as well, and hence the gas concentration cannot be measured accurately in that case.

Figure 9:
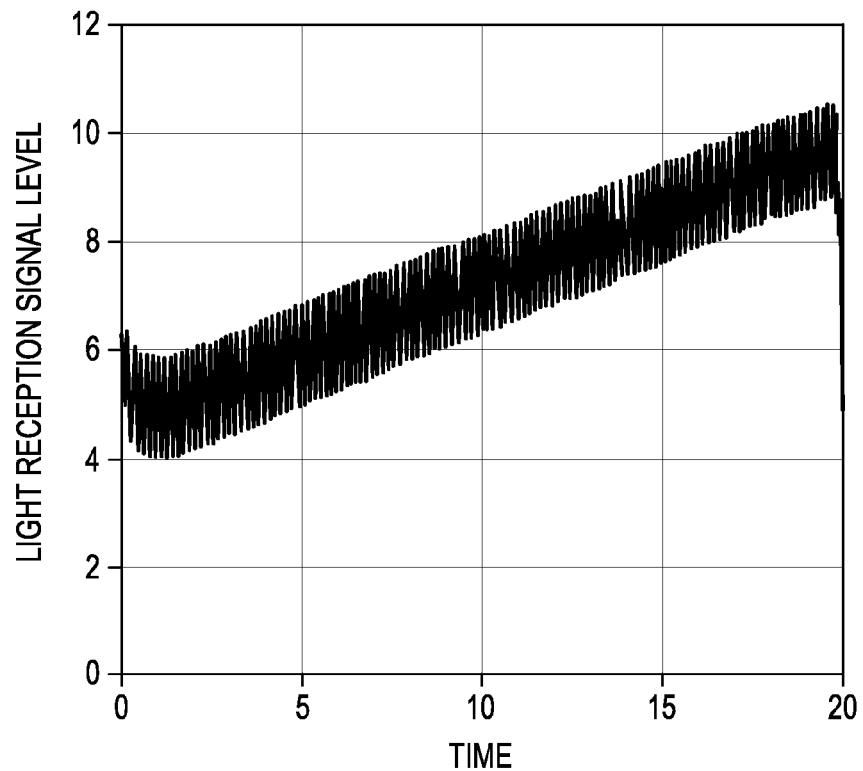
FIG. 9 is a light reception signal waveform diagram in a dust-free environment.
Figure 10:
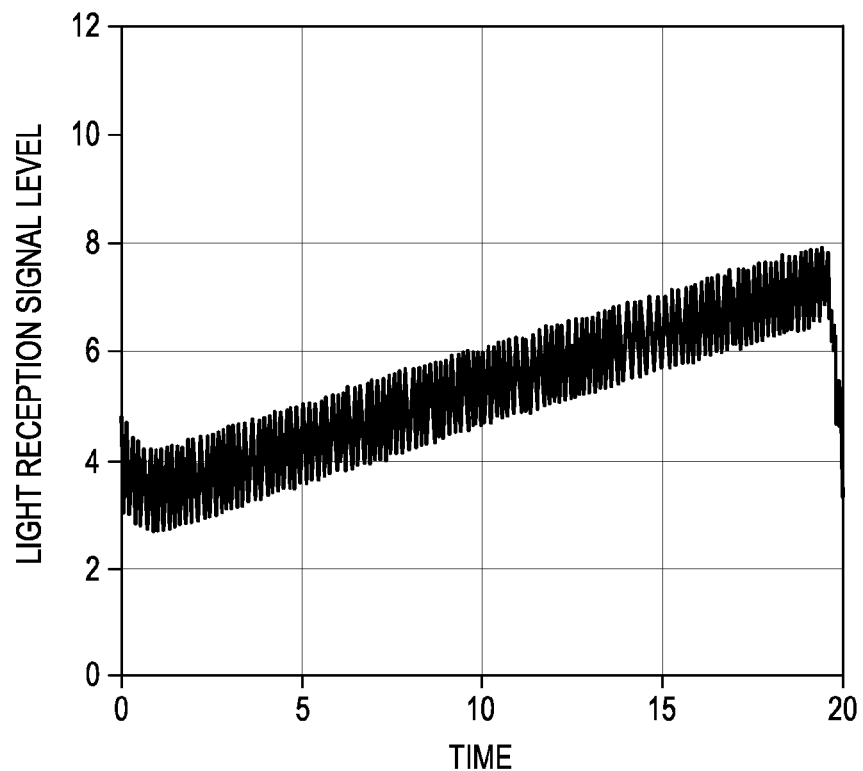
FIG. 10 is a light reception signal waveform diagram in an environment where dust is present.
Figure 12:
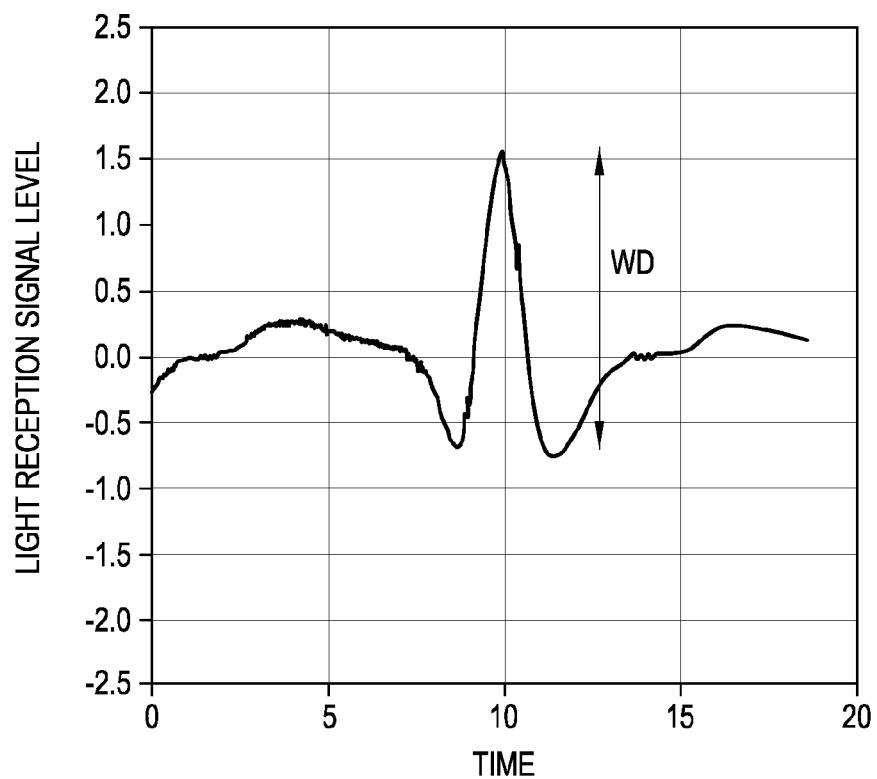
FIG. 12 is an output waveform diagram with absorption in an environment where dust is present.

Assuming for instance that a light reception signal and a peak value such as those illustrated in FIG. 9 and FIG. 11 are obtained in a dust-free environment, then the gas concentration can be measured through detection of the amplitude W ($=W_A$) of the relevant waveform. In an environment where dust is present, by contrast, the light reception signal level drops, as illustrated in FIG. 10 and FIG. 12, and the amplitude W ($=W_D$) of the peak value decreases as well. This precludes accurate detection of the gas concentration.

Figure 14:
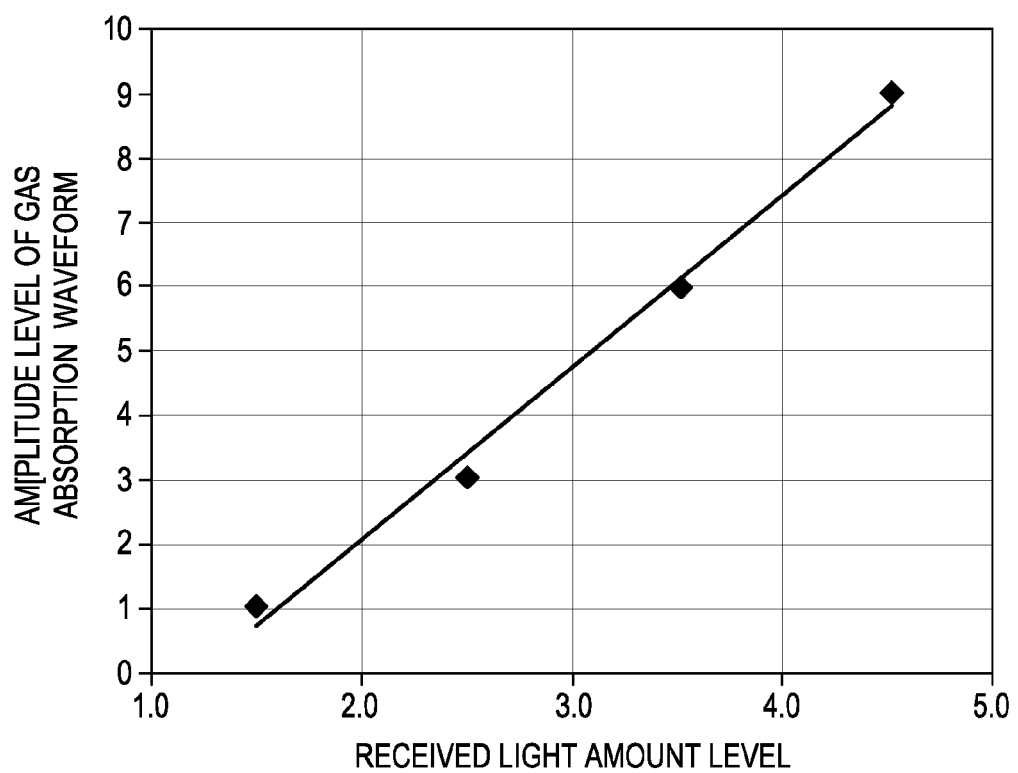
FIG. 14 is a characteristic diagram illustrating the relationship between received light amount level and amplitude level of a gas absorption waveform.

Focusing on the substantially proportional relationship between the received light amount level and the gas absorption waveform, as illustrated in FIG. 14, the gas concentration can therefore be detected accurately also in an environment where dust or the like is present, through calculation of the received light amount for calculating a correction coefficient, in the near-infrared light reception signal processing and computing unit 23, and through correction in the gas concentration correcting unit 24.

Figure 25:
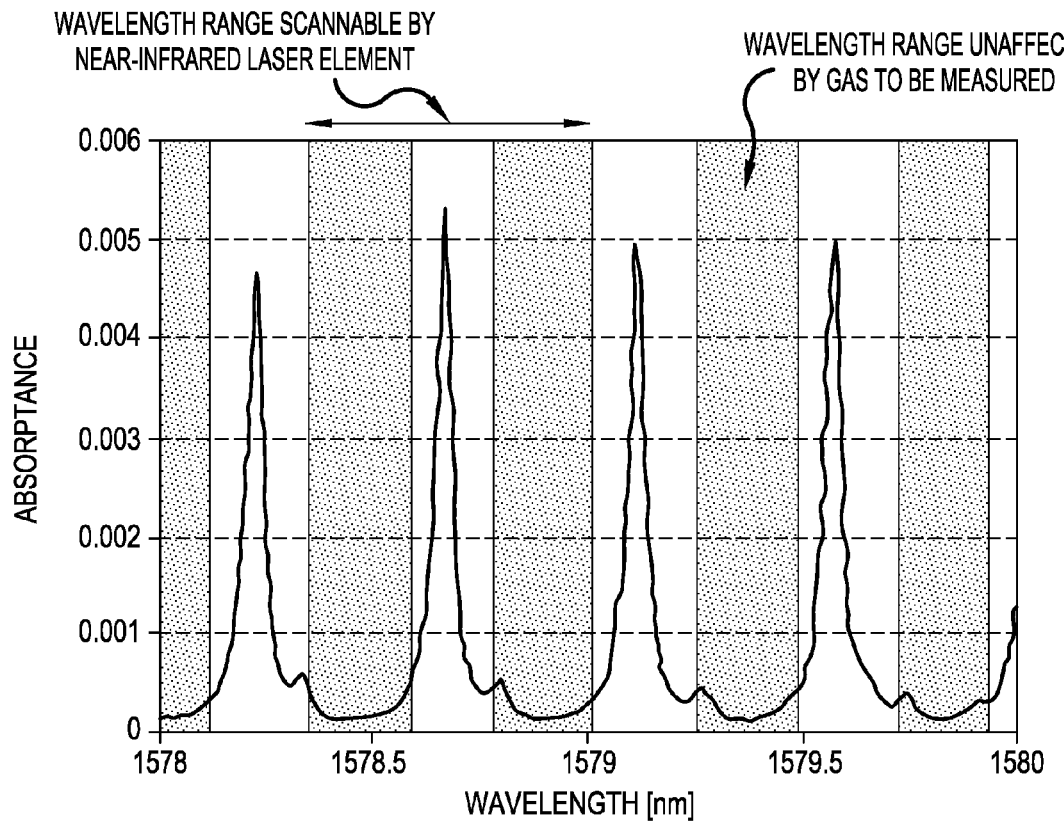
FIG. 25 is a diagram illustrating a spectral characteristic of $CO_2$ gas.
Figure 26:
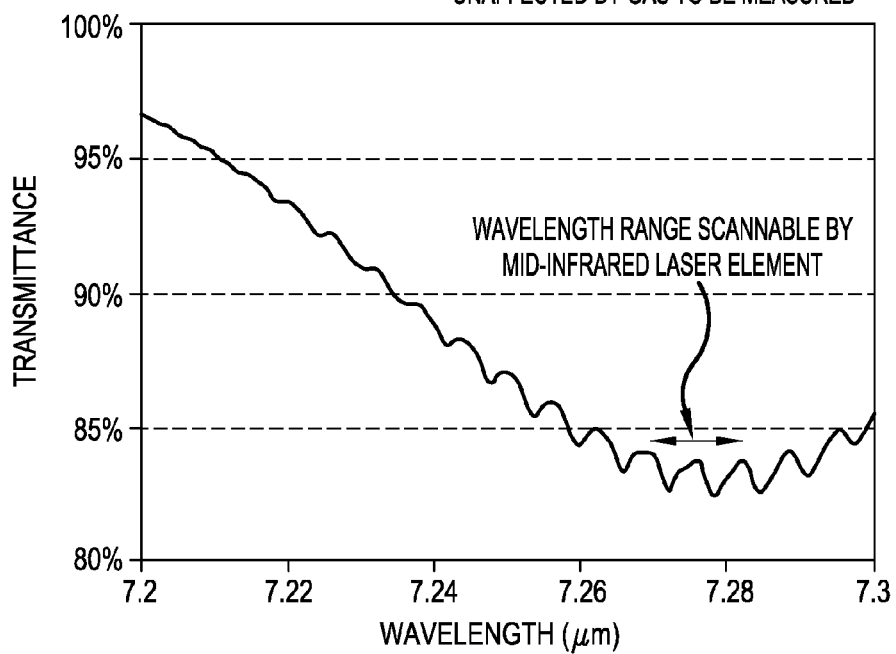
FIG. 26 is a diagram illustrating a spectral characteristic of $SO_2$ gas.

Scanning of the second wavelength band by the near-infrared laser driving unit 21 involves herein continuously scanning of the absorption wavelengths of $CO_2$ gas and scanning for light amount decrement detection. Modulation of near-infrared laser light is identical to modulation of mid-infrared light laser. Herein there is used the output signal of the wavelength scanning drive signal generating unit 20a of FIG. 13(b). The wavelength band is set in such a manner that $CO_2$ gas can be detected at the wavelength of point a, and the light amount decrement can be detected at the wavelength of point b. (Point a is a peak point of a white background region of the characteristic in FIG. 25, and the point b is a lowermost point of a shaded region of the characteristic in FIG. 25.)

Upon input, to the laser drive signal generating unit 20c, of the wavelength scanning drive signal generating unit 20a for modifying the emission wavelength of the laser thus adjusted, and of the output signal of the high-frequency modulated signal generating unit 20b for frequency modulation of the emission wavelength, for instance with a sine wave of about 20 kHz, for detecting the absorption waveform of $CO_2$ gas, the laser drive signal generating unit 20c combines these output signals to generate thereby a drive signal. A drive signal such as the one of the waveform diagram of the drive signal outputted by the laser drive signal generating unit 20c of FIG. 6 (composite signal of the output signal of the wavelength scanning drive signal generating unit 20a and the output signal of the high-frequency modulated signal generating unit 20b) is subjected to V-I conversion in the laser drive signal generating unit 20c, and is supplied to the near-infrared laser element 8a.

From the near-infrared laser element 8a there is emitted, as a result, the first laser light of a predetermined wavelength band having been frequency-modulated with scanning, with a wavelength width of about 0.2 nm, of the absorption characteristic of the second gas to be measured ($CO_2$ gas) for about several nm, and there is emitted third laser light of a predetermined wavelength band for acquisition of a signal for light amount decrement detection. As illustrated in FIG. 1, the laser light emitted by the near-infrared laser element 8a passes through a central hole of the concave mirror 10, and is emitted in the form of the parallel near-infrared laser light 17. The temperature of the near-infrared laser element 8a is adjusted beforehand in such a manner that the gas is measured at the central portion of the wavelength scanning drive signal. As a result there is emitted laser light of a wavelength of the near-infrared region that includes the optical absorption spectrum of $CO_2$ gas and a wavelength for light amount decrement detection.

Such near-infrared laser light 17 propagates through the flue interior, being the interior zone between the flue walls 101a, 101b (space through which the gas to be measured flows), and is absorbed by $CO_2$ gas as the laser light passes through this space. The operation and function of the near-infrared laser driving unit, near-infrared laser light-emitting unit and the near-infrared laser optical unit of the present invention are thus as described above.

The near-infrared light-receiving unit of the present invention will be explained next. The first and third laser light are outputted continuously, and signal processing is performed likewise continuously, for the second wavelength band. For the sake of clarity in the explanation, signal processing upon reception of the first laser light will be explained first.

In the detection light having propagated through that space in which $SO_2$ gas, $CO_2$ gas, water and dust are present, laser light of a wavelength of the near-infrared region, including the optical absorption spectrum of $CO_2$ gas by the first laser light, undergoes absorption by $CO_2$ gas. This detection light passes through the aperture 16 of the concave mirror 15, is thereafter condensed by the lens 14, and is then received by the near-infrared light-receiving element 13. The near-infrared light-receiving element 13 outputs a detection signal, in the form of an electric signal, in response to the received light amount. The near-infrared light-receiving element 13 is for instance a photodiode. An element is used herein that has sensitivity towards the laser emission wavelength.

In the case of absorption by $CO_2$ gas, next, the detection signal that is inputted from the near-infrared light-receiving element 13 to the near-infrared light reception signal processing and computing unit 23 is initially converted first from a current signal to a voltage signal by the I/V conversion unit 22a, in the near-infrared light reception signal processing and computing unit 23. This voltage signal as well has an output waveform such as the one illustrated in FIG. 9. This voltage signal is inputted to the synchronous detecting unit 22b. The reference signal generating unit (oscillator) 22c outputs, to the synchronous detecting unit 22b, a reference signal in the form of a double frequency signal of the high-frequency modulated signal by the high-frequency modulated signal generating unit 20b (FIG. 3). Only the amplitude of the double frequency component of the modulated signal is extracted in the synchronous detecting unit 22b. The measurement is performed on the basis of the concentration measurement principle according to the frequency modulation method of FIG. 22 explained above.

After noise removal at the filter unit 22d, the signal is inputted to the computing unit 22e. The computing unit 22e calculates the gas concentration of the $CO_2$ gas using this signal. This signal takes on a value proportional to the concentration of $CO_2$ gas, and has a peak value such as the one illustrated in FIG. 11. The computing unit 22e may calculate the peak amplitude and may integrate the signal change, to compute the gas concentration from the peak value.

In one example, the computing unit 22e can detect the gas concentration by multiplying the amplitude $W_C$ of such a synchronous detection signal such as the one illustrated in FIG. 11, by a given span calibration value $G_C$ for $CO_2$ gas concentration and by a gas temperature correction coefficient $\alpha_C$.

$$\text{Concentration of } CO_2 \text{ gas} = \alpha_C \times G_C \times W_A \qquad [\text{Math. 4}]$$

It suffices that the gas temperature correction coefficient $\alpha_C$ be a coefficient that is determined uniquely for the gas temperature of $CO_2$ gas. The form of the gas temperature correction coefficient $\alpha_C$ is not limited, and the latter may take a function form or a table form.

The $CO_2$ gas concentration must be corrected since, although little affected by water, it is affected by the light amount decrease due to dust. The computing unit 22e sends the $CO_2$ gas concentration to the gas concentration correcting unit 24. The process performed by the gas concentration correcting unit 24 will be explained further on.

Signal processing for the second wavelength band upon reception of the third laser light will be explained next. In the detection light having propagated through a space in which $SO_2$ gas, $CO_2$ gas, water and dust are present, the third laser light, of a wavelength of a near-infrared region that does not include the optical absorption spectra of $CO_2$ gas and $SO_2$ gas, undergoes no absorption by gas but only light amount decrease due to dust. This detection light passes through the aperture 16 of the concave mirror 15, is then condensed by the lens 14, and is thereafter received by the near-infrared light-receiving element 13. The near-infrared light-receiving element 13 outputs a detection signal, in the form of an electric signal, in response to the received light amount. The near-infrared light-receiving element 13 is for instance a photodiode. An element is used herein that has sensitivity towards the laser emission wavelength.

In a case of light amount decrease due to dust, next, the detection signal inputted from the near-infrared light-receiving element 13 to the near-infrared light reception signal processing and computing unit 23 is converted, by the I/V conversion unit 22a of the near-infrared light reception signal processing and computing unit 23, from a current signal to a voltage signal. The voltage signal has an output waveform such as the one illustrated in FIG. 10. This voltage signal is inputted to the synchronous detecting unit 22b. The reference signal generating unit (oscillator) 22c outputs, to the synchronous detecting unit 22b, a reference signal in the form of a double frequency signal of the high-frequency modulated signal by the high-frequency modulated signal generating unit 20b (FIG. 3). Only the amplitude of the double frequency component of the modulated signal is extracted in the synchronous detecting unit 22b. The measurement is performed on the basis of the concentration measurement principle according to the frequency modulation method of FIG. 22 explained above.

Figure 16:
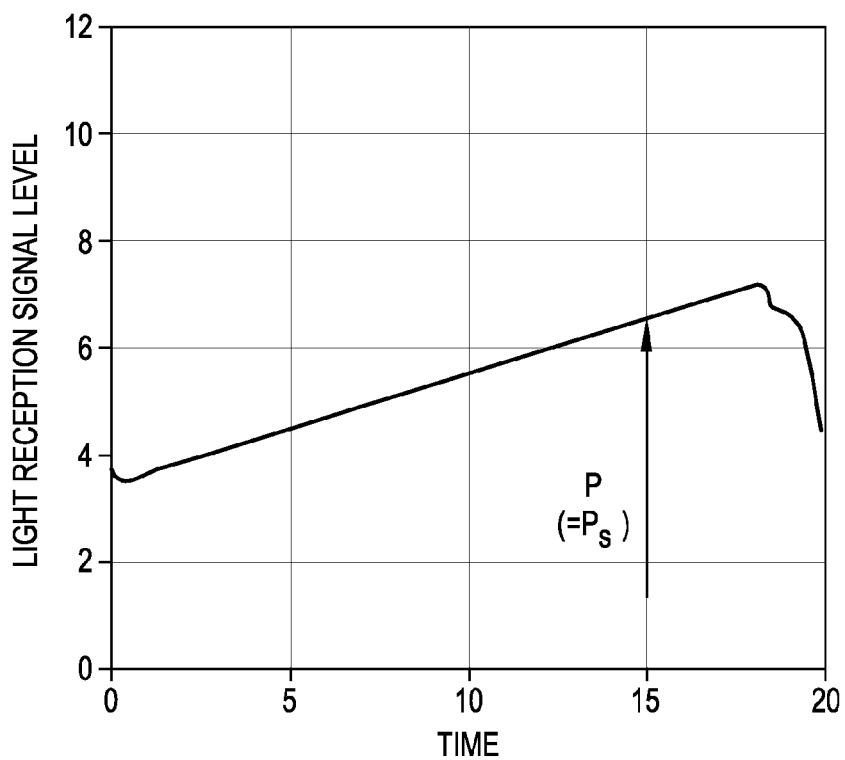
FIG. 16 is an output waveform diagram in the absence of absorption in an environment where dust is present.

After noise removal at the filter unit 22d, the signal is inputted to the computing unit 22e. This signal takes on a value, which is unaffected gas or water absorption but proportional to the light amount decrease due to scattering by dust, and exhibits a waveform as shown in FIG. 16. In the computing unit 22e there is calculated a light amount decrement P at time 15. The computing unit 22e sends the light amount decrement to the gas concentration correcting unit 24. The process performed by the gas concentration correcting unit 24 will be explained below.

The correction process by the gas concentration correcting unit 24 will be explained next. The gas concentration correcting unit 24 corrects the gas concentration of the first gas to be measured ($SO_2$ gas) worked out by the mid-infrared light reception signal processing and computing unit 22, and the gas concentration of the second gas to be measured ($CO_2$ gas) worked out by the near-infrared light reception signal processing and computing unit 23, using the water concentration and the light amount decrement that are worked out by the near-infrared light reception signal processing and computing unit 23. More specifically, the concentration of $SO_2$ gas is corrected by the water concentration and the light amount decrement, and the concentration of $CO_2$ gas is corrected by the light amount decrement.

Figure 17:
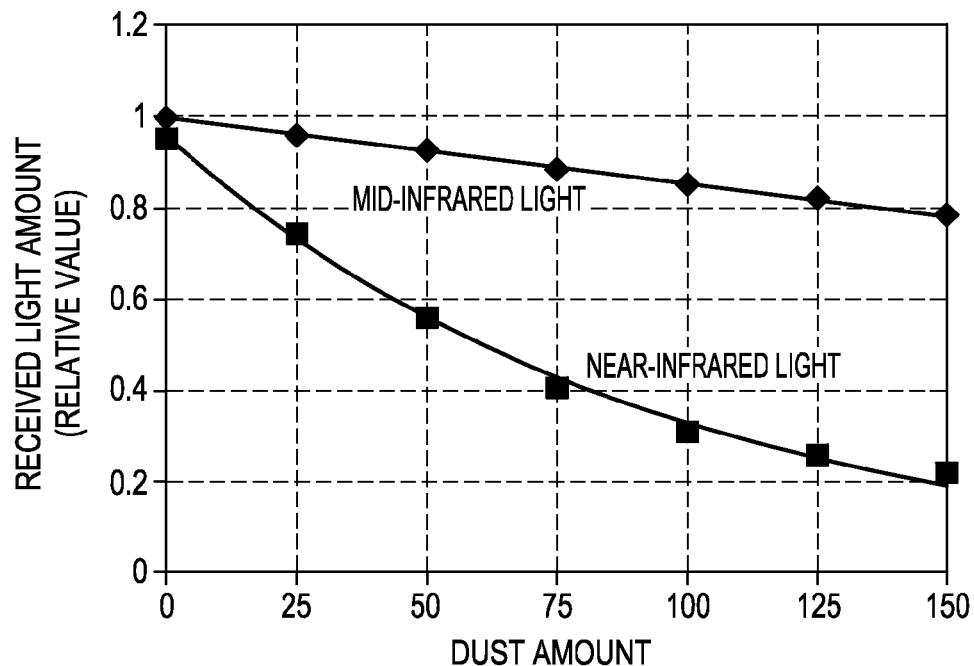
FIG. 17 is a characteristic diagram illustrating the relationship between received light amount of near-infrared light and received light amount of mid-infrared light, with respect to dust amount.

Light amount correction will be explained in detail first. The change in the received light amount of near-infrared light and mid-infrared light with respect to the dust amount behaves as depicted in FIG. 17. In near-infrared light, in particular, the received light amount decreases significantly as the dust amount increases. The light amount decrement is calculated, on the basis of this value, using the following expression.

$$\text{Light amount decrement} = -\log \text{(received light amount relative value)} \qquad [\text{Math. 5}]$$

Figure 18:
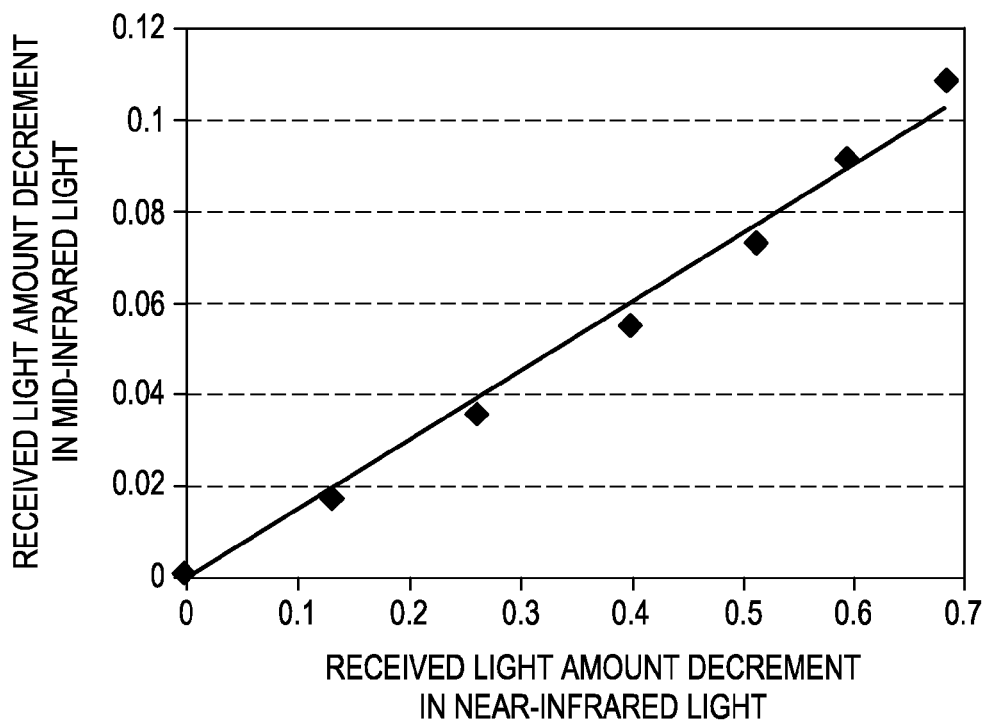
FIG. 18 is a characteristic diagram illustrating the relationship between a received light amount decrement of near-infrared light and a received light amount decrement of mid-infrared light.

A correlation between the near-infrared light amount decrement and the mid-infrared light amount decrement yields a graph such as the one in FIG. 18, which reveals a strong correlation in the characteristic of light amount decrease for dust between near-infrared light and mid-infrared light. Therefore, the received light amount of mid-infrared light that is reduced due to dust can be estimated on the basis of the near-infrared light received light amount that is reduced due to dust.

Figure 15:
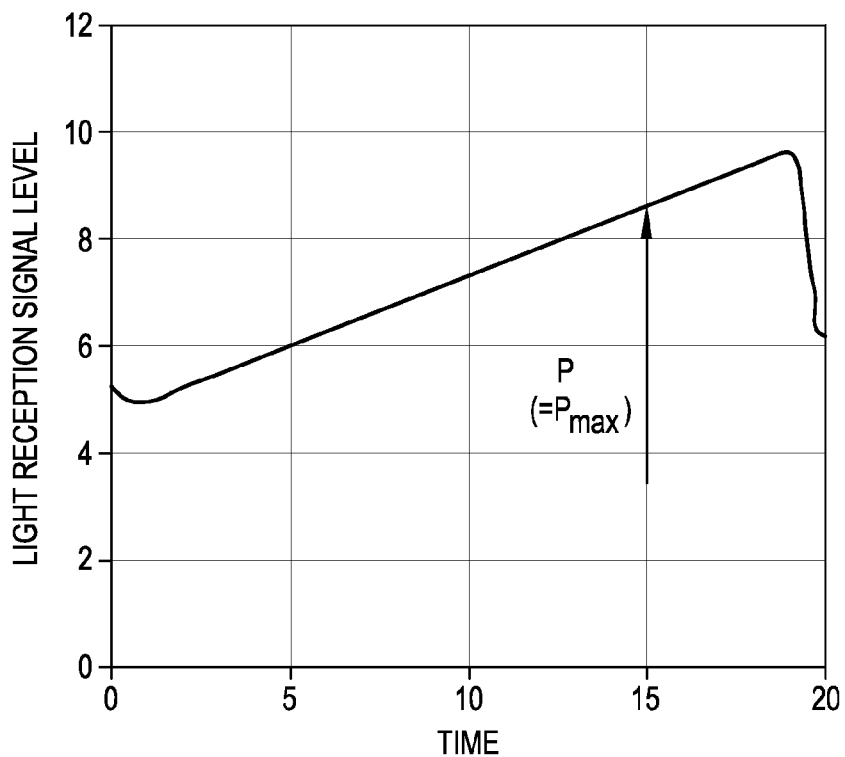
FIG. 15 is an output waveform diagram in the absence of absorption in a dust-free environment.

In detection of the light amount decrement, waveforms such as the those illustrated in FIG. 15 and FIG. 16 are obtained upon extraction of the wavelength scanning drive signal component as the light reception signals illustrated in FIG. 9 and FIG. 10 pass through the synchronous detecting unit 22b and filter unit 22d of the near-infrared light reception signal processing and computing unit 23. FIG. 15 corresponds to an instance where dust is absent, and the received light amount does not decrease, and FIG. 16 corresponds to an instance where dust is present and the received light amount drops accordingly. The position of time 15 for near-infrared light in FIG. 15 and FIG. 16, is unaffected by $CO_2$ gas, as in point b in FIG. 13, (see portion (b)), and, accordingly, it becomes possible to detect the decrease due to the influence of dust alone.

As illustrated in FIG. 15, a level $P_{max}$ of light reception signal at a time where there is no dust and the received light amount is maximal, i.e. at the time of factory shipping or upon calibration, is set beforehand in the computing unit 22e as a received light amount set value. The computing unit 22e detects a light reception signal level Ps of an instance where dust is present (instance of reduction in the light amount as worked out using the third laser light), as illustrated in FIG. 16, and outputs the light reception signal level Ps, as a light amount decrement, to the gas concentration correcting unit 24. The gas concentration correcting unit 24 calculates a ratio of Ps and $P_{max}$ of a same point in time, as a received light amount correction coefficient β, according to Expression 6 below.

$$\beta = P_{max}/P_s \quad \text{[Math. 6]}$$

The gas concentration corrected for the variation of received light amount due to dust can be then obtained in the gas concentration correcting unit 24 through multiplication or division of the gas concentration by the received light amount correction coefficient β, as in Expression 7 below.

Concentration of the gas to be measured (after correction)=β×concentration of the gas to be measured (before correction)=$P_{max}/P_s$×concentration of the gas to be measured (before correction) [Math. 7]

The foregoing can be expressed as given in the expressions below, substituting Expressions 2 and 4 explained above.

Concentration of $SO_2$ gas (after correction)=$\alpha_A \times G_A \times W_A \times P_{max}/P_s$ [Math. 8]

Concentration of $CO_2$ gas (after correction)=$\alpha_B \times G_B \times W_B \times P_{max}/P_s$ [Math. 9]

The gas concentration correcting unit 24 performs the above corrections for the concentration of $SO_2$ gas the concentration of $CO_2$ gas, respectively. Next, the gas concentration measured value of $SO_2$ gas worked out above is corrected on the basis of the water concentration. As the correction method, the gas concentration measured value of $SO_2$ gas worked out previously may be corrected using an already-known decrement of a gas concentration measured value according to the light amount decrement by water concentration, since the degree to which the gas concentration measured value decreases according to the water concentration in the space to be measured can be measured beforehand. The light amount decrement by water concentration can be calculated in accordance with the same method as that of the light amount decrement by dust.

For instance, the light amount of mid-infrared light is assumed to vary according to a given function f with respect to water concentration.

$$\gamma = f(\text{water concentration}) \quad \text{[Math. 10]}$$

Herein, γ is a received light amount correction coefficient by water.

The gas concentration correcting unit 24 calculates the received light amount correction coefficient γ using the water concentration as outputted by the near-infrared light reception signal processing and computing unit 23. The gas concentration corrected for the variation in the received light amount due to water can be obtained in the gas concentration correcting unit 24, through multiplication or division of the concentration of $SO_2$ gas (after correction) by the received light amount correction coefficient γ, as in the expression below.

Concentration of $SO_2$ gas (after correction)=$\alpha_A \times G_A \times W_A \times \gamma \times P_{max}/P_s$ [Math. 11]

The concentration of $SO_2$ gas (see Expression 11 above) and the concentration of $CO_2$ gas (see Expression 9 above) after such corrections are sent to a subsequent output unit. The output unit is for instance a display device or a warning device, or a transmitting device for transmission to another computer. Detection of the gas to be measured according to a frequency modulation method is thus accomplished as described above. Thus, accurate gas concentration measurement of $SO_2$ and $CO_2$ is made possible, even upon fluctuation of the received light amount due to dust, through calculation of a gas concentration corrected for the decrement of light amount, as described above.

Figure 19:
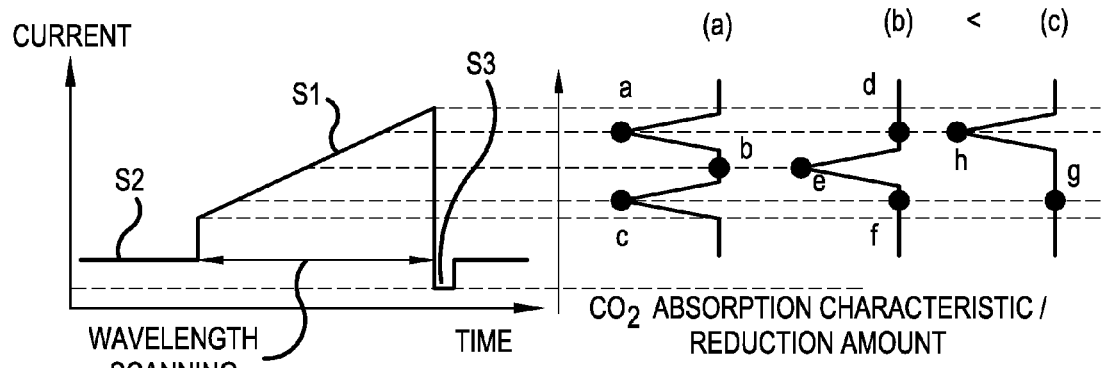
FIG. 19 is an explanatory diagram of another relationship between emission wavelength and detection wavelength in a laser element.
Figure 20:
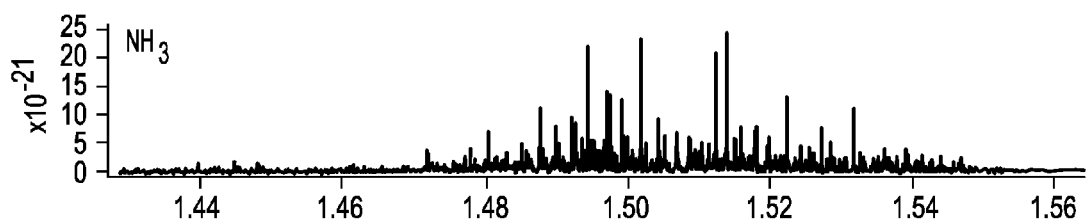
FIG. 20 is a diagram illustrating the optical absorption spectrum of ammonia ($NH_3$)
Figure 21:
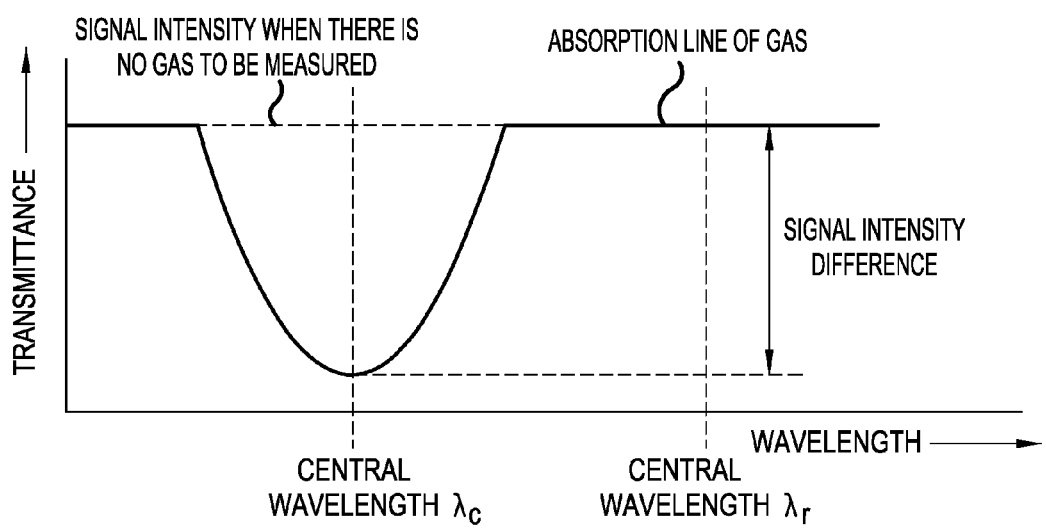
FIG. 21 is a diagram illustrating a concentration measurement principle according to a differential absorption method.

The present invention has been explained above, but the invention may accommodate all manner of variations. For instance, the second wavelength sweep band is set for detection at a timing such as the one illustrated in FIG. 13 (see portion (b)) explained above, but it is possible to set wavelength bands for detection at various timings, for instance, detection of $CO_2$ gas at points a and c on both sides of the wavelength, and detection of the light amount decrement, at point b in the wavelength center, as illustrated in FIG. 19 (see portion(a)), detection of $CO_2$ gas at point e in the wavelength center and detection of the light amount decrement at points d and f on both sides of the wavelength, as illustrated in FIG. 19 (see portion(b)), or detection of the $CO_2$ gas at point h on one side of the wavelength and detection of the light amount decrement at point g on the other side of the wavelength, as illustrated in FIG. 19 (see portion (c)).

In the embodiments, $SO_2$ gas is measured in a mid-infrared region and $CO_2$ gas in a near-infrared region, but it is also possible to measure NO gas, $NO_2$ gas or the like in a mid-infrared region, and $NH_3$ gas and HCl gas in a near-infrared region. In uses other than marine exhaust gas analysis, the laser-type gas analyzer may be a laser-type gas analyzer in which the foregoing gases are selected/combined as the first and second gases to be measured. An optimal wavelength for the first gas to be measured is selected from 3 to 10 μm in the mid-infrared region, for the wavelength of laser light. An optimal wavelength for the second gas to be measured is selected from 0.7 to 3 for the wavelength of laser light in the near-infrared region.

As measurement timings, $SO_2$ gas may be set to be measured in the mid-infrared region at a timing simultaneous with the timing of measurement of $CO_2$ gas in the near-infrared region, so as to cause the distribution conditions of dust and water in the flue to coincide at identical points in time.

Focusing on the feature wherein a $S_3$ signal such as the one illustrated in FIG. 5 and FIG. 6 is outputted every period in the laser-type gas analyzer of the present invention, the peak value of the output waveform in the synchronous detecting unit appears once a predetermined time has elapsed since detection of the $S_3$ signal. Concentrations may thus be set to be calculated at this timing.

The embodiments involve measurement of concentration, but may involve also detection of the presence or absence of the gas to be measured, by determining that the gas to be measured is absent if the concentration thereof is virtually zero.

In the embodiments, the optical paths of the mid-infrared light and the near-infrared light coincide with each other, but a configuration may be resorted to wherein the optical paths are separate. Preferably, however, the optical path in gas analysis and the optical path in measurement of the light amount decrease due to dust coincide with each other, since the distributions of dust and water in the flue are not necessarily uniform.

In the embodiments, the near-infrared laser light 17 may be set to pass through the interior of the mid-infrared laser light 2, coaxially with the latter. The mid-infrared laser light 2 may be set herein to pass coaxially through the interior of the near-infrared laser light 17, for instance by reversing the arrangement of the mid-infrared laser light-emitting unit 7 and the near-infrared laser light-emitting unit 8.

Aside from the arrangement of the light-emitting units 7, 8, the present invention is not limited to the above-described embodiments, and may accommodate many other variations without departing from the essence of the invention.

In the present invention, instances have been explained wherein emission and detection are each performed at matched timings, but, for instance, a CPU not shown may be connected to the mid-infrared laser driving unit 20, the near-infrared laser driving unit 21, the mid-infrared light reception signal processing and computing unit 22, the near-infrared light reception signal processing and computing unit 23 and the gas concentration correcting unit 24, such that the CPU performs operation control and computations relating to emission and detection while adjusting the respective timings.

The present invention allows measuring, under identical conditions, a light amount decrement on the optical path of gas concentration measurement, by resorting to an optical system that emits coaxially laser light of a wavelength at which there is absorption by $CO_2$ gas and laser light of a wavelength at which there is absorption by $SO_2$ gas; it becomes thus possible to measure accurately the concentration of $SO_2$ gas having an absorption spectrum over the entire laser light wavelength scanning range, and to measure $CO_2$ gas at the same time.

Even if water is present at a high concentration in a space to be measured, such as a flue interior, gas concentration measured values can be corrected by measurement of the water concentration using the near-infrared laser light 17. Accordingly, it becomes possible to measure, with high precision, the concentration of the gases to be measured.

The laser-type gas analyzer of the present invention is optimal for measurement of combustion exhaust gas in boilers, waste incineration and the like. The laser-type gas analyzer of the present invention can also be used, for instance, in gas analysis for iron and steel [blast furnaces, converter furnaces, heat treatment furnaces, sintering (pelleting facilities), coke furnaces]; fruit and vegetable storage and ripening, biochemistry (microorganisms) [fermentation]; air pollution [incinerators, flue gas desulfurization and denitration]; automotive emissions (excluding testers), disaster prevention [explosive gas detection, toxic gas detection, combustion gas analysis in new building materials]; plant growth, chemical analysis [petroleum refineries, petrochemical plants, gas generation plants]; the environment [landing concentration, tunnel concentration, parking areas, building management]; as well as in various experiments in chemistry and physics.

What is claimed is:

1. A laser-type gas analyzer, comprising:
    a mid-infrared laser light-emitting unit that emits laser light of a wavelength band of a mid-infrared region that includes an optical absorption spectrum of a first gas to be measured;
    a mid-infrared laser driving unit that drives the mid-infrared laser light-emitting unit;
    a mid-infrared laser optical unit that collimates the laser light emitted by the mid-infrared laser light-emitting unit, and irradiates the light into a space to be measured in which the first gas to be measured is present;
    a mid-infrared light-receiving unit that receives the laser light irradiated by the mid-infrared laser optical unit, and outputs the received laser light as an electrical mid-infrared light reception signal;
    a mid-infrared light reception signal processing and computing unit that extracts, from the mid-infrared light reception signal, a signal component affected by optical absorption by the first gas to be measured, and calculates a gas concentration of the first gas to be measured on the basis of an amount of change of this signal component;
    a near-infrared laser light-emitting unit that emits, at respective times, first laser light of a wavelength band of a near-infrared region that includes an optical absorption spectrum of a second gas to be measured, second laser light of a wavelength band of a near-infrared region that includes an optical absorption spectrum of water, and third laser light of a wavelength band of a near-infrared region in which the optical absorption spectra of water, the first gas to be measured and the second gas to be measured are equal to or smaller than a predetermined amount;
    a near-infrared laser driving unit that drives the near-infrared laser light-emitting unit;
    a near-infrared laser optical unit that collimates, at respective times, the first, second and third laser light emitted by the near-infrared laser light-emitting unit, and irradiates the collimated light to the space to be measured;
    a near-infrared light-receiving unit that receives, at respective times, the first, second and third laser light irradiated by the near-infrared laser optical unit, and outputs the received light as respective electrical near-infrared light reception signals;
    a near-infrared light reception signal processing and computing unit that performs, at respective times, processes of extracting, from the near-infrared light reception signal of the first laser light, a signal component affected by optical absorption by the second gas to be measured, and computing a gas concentration of the second gas to be measured on the basis of an amount of change of this signal component, computing a water concentration in the space on the basis of the near-infrared light reception signal of the second laser light, and computing a light amount decrement due to dust on the basis of the near-infrared light reception signal of the third laser light; and
    a gas concentration correcting unit that corrects the gas concentration of the first gas to be measured, as worked out by the mid-infrared light reception signal processing and computing unit and the gas concentration of the second gas to be measured, as worked out by the near-infrared light reception signal processing and computing unit, in use of the water concentration and light amount decrement as worked out by the near-infrared light reception signal processing and computing unit.

2. The laser-type gas analyzer according to claim 1, wherein the first gas to be measured is $SO_2$ gas and the second gas to be measured is $CO_2$ gas.

3. The laser-type gas analyzer according to claim 2, wherein the wavelength of laser light of the mid-infrared region emitted by the mid-infrared laser light-emitting unit ranges from 3 to 10 µm, and the wavelength of the laser light of the near-infrared region emitted by the near-infrared laser light-emitting unit ranges from 0.7 to 3 µm.

* * * * *